United States Patent [19]

Haseyama et al.

[11] Patent Number: 5,126,426
[45] Date of Patent: Jun. 30, 1992

[54] ALICYCLIC DIAMINES, ALICYCLIC DIISOCYANATES AND POLYISOCYANATO-ISOCYANURATES AND METHOD FOR THE PREPARATION THEREOF

[75] Inventors: Ryuji Haseyama; Masatoshi Takagi; Kouzou Hayashi; Katsuyoshi Sasagawa; Kazuyuki Kuroda; Taisaku Kano, all of Kanagawa; Kiyoshi Shikai, Tokyo, all of Japan

[73] Assignee: Mitsui Toatsu Chemicals, Incorporated, Tokyo, Japan

[21] Appl. No.: 511,183

[22] Filed: Apr. 19, 1990

[30] Foreign Application Priority Data

Apr. 21, 1989 [JP] Japan .................................. 1-100121
May 8, 1989 [JP] Japan .................................. 1-113820

[51] Int. Cl.⁵ .......................................... C08G 18/75
[52] U.S. Cl. .......................................... 528/73; 564/450; 564/451; 564/453; 564/455; 564/461; 564/462
[58] Field of Search ............... 564/450, 451, 453, 455, 564/461, 462; 528/73

[56] References Cited

U.S. PATENT DOCUMENTS

| | | | |
|---|---|---|---|
| 3,636,108 | 1/1972 | Brake | 564/451 |
| 4,193,905 | 3/1980 | Audykowski et al. | 528/124 |
| 4,582,888 | 4/1986 | Kase et al. | 528/49 |

FOREIGN PATENT DOCUMENTS

| | | |
|---|---|---|
| 2132547 | 1/1973 | Fed. Rep. of Germany . |
| 2353151 | 4/1974 | Fed. Rep. of Germany . |
| 3326579 | 1/1985 | Fed. Rep. of Germany . |
| 3507719 | 9/1986 | Fed. Rep. of Germany . |

OTHER PUBLICATIONS

Derwent Japanese Patent Abstracts-vol. 14 (No. 36), 20178/65 Asahi Chem. Ind. Co., Aug. 9 1963.
Patent Abstracts of Japan, Unexamined Applications, Section C, vol. 3, No. 43, Apr. 13, 1979.

*Primary Examiner*—Maurice J. Welsh
*Assistant Examiner*—Rachel Johnson

*Attorney, Agent, or Firm*—Burns, Doane, Swecker & Mathis

[57] ABSTRACT

Herein disclosed are an α-(aminocyclohexyl)alkylamine represented by the following general formula (II):

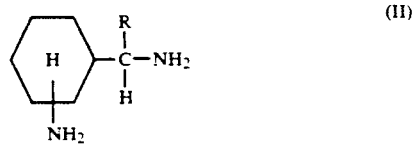

(II)

wherein R represents hydrogen atom or a lower alkyl group having 1 to 5 carbon atoms, provided that the amino group bonded to the cyclohexyl group may be in either of the 2-, 3- and 4-positions and a method for preparing it; an α-(isocyanatocyclohexyl)alkylisocyanate of Formula (II) wherein the amino groups are replaced with isocyanato groups and a method for preparing it; polyisocyanato-isocyanurate represented by the following general formula (IV):

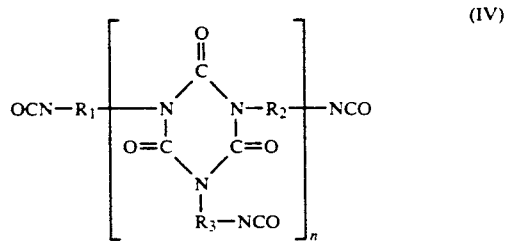

(IV)

wherein $R_1$, $R_2$ and $R_3$ may be the same or different and each represents a group represented by the following general formula:

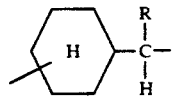

wherein R represents hydrogen atom or an alkyl group
(List continued on next page.)

having 1 to 5 carbon atoms and n is an integer ranging from 1 to 5 and a method for preparing it; and a resin obtained by polymerizing an organic polyisocyanate containing not lower than 10% by weight of the polyisocyanato-isocyanurate represented by Formula (IV) and a compound having at least two active hydrogen atoms as well as a resin composition for coating materials which comprises the resin.

5 Claims, 4 Drawing Sheets

ALICYCLIC DIAMINES, ALICYCLIC DIISOCYANATES AND POLYISOCYANATO-ISOCYANURATES AND METHOD FOR THE PREPARATION THEREOF

BACKGROUND OF THE INVENTION

1. Field of the Invention

The present invention relates to alicyclic diamines, alicyclic diisocyanates and polyisocyanato-isocyanurates as well as a method for the preparation of these compounds and the use thereof as isocyanate components. The alicyclic diamines, alicyclic diisocyanates and polyisocyanato-isocyanurates are each compounds having a novel structure and the alicyclic diamines can be used as hardening agents for epoxy resins, polyurethanes and polyureas as well as starting materials for preparing polyamides. The alicyclic diisocyanates can widely be used in various fields, for instance, in expandable materials, elastic materials, synthetic leathers, coating materials, adhesives, films and fibers as well as starting materials for polyurethane resins, polyurea resins and polyamides. Moreover, the polyisocyanato-isocyanurates can be used as expandable materials, adhesives and resins for coating materials as well as starting materials therefor.

2. Description of the Prior Art

An example of alicyclic diamines which have conventionally been well-known is bis(aminomethyl)cyclohexane (hereinafter referred to as "H$_6$-XDA") represented by the following formula (a):

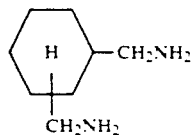

This compound has widely been employed in various fields as a starting material for epoxy resins and polyamides.

An example of alicyclic diisocyanates which have conventionally been well-known is bis(isocyanatomethyl)cyclohexane represented by the following formula (b) (hereinafter referred to as "H$_6$-XDI"):

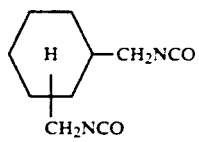

This compound has widely been used in various fields as a starting material for polyurea resins and the like.

In addition, an example of polyisocyanato-isocyanurates which have conventionally been well-known is an isocyanurate of hexamethylene diisocyanate represented by the following formula (c):

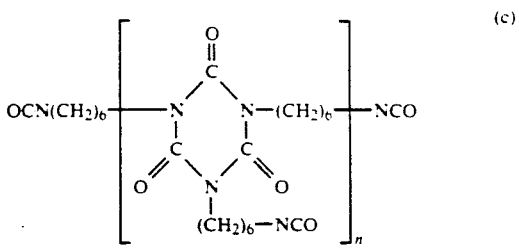

This has been widely used in various fields as a resin for two-pack urethane coating materials as well as a starting material for the resin.

Saunders Frisch (High Polymers, Vol. XVI, "Polyurethanes: Chemistry and Technology II, Technology", p. 453) ptoposes resins which comprise, as chief materials, alkyd resins, polyester polyols, acryl polyols or epoxy polyols and, as a hardening agent, an urethane type polyisocyanate derived from tolylene diisocyanate or an isocyanurate type polyisocyanate, as typical examples of the most general-purpose resins for two-pack urethane coating materials. These resins have been used not only in coating materials for furniture and woodworking, but also in coating materials for heavy duty anticorrosion so-called tar-urethane paints. However, urethane coating materials obtained from tolylene diisocyanate show substantially low weatherability.

In order to enhance the weatherability of these resins for coating materials, there have been proposed the use of urethane type polyisocyanates derived from hexamethylene diisocyanate (HDI) (see, for instance, Japanese Patent Publication for Opposition Purpose (hereunder referre to as "J. P. KOKOKU") No. Sho 45-11146); biuret type polyisocyanates (see, for instance, U.S. Pat. No. 3,903,127); isocyanurate type polyisocyanates (see, for instance, U.S. Pat. Nos. 3,487,080, 4,324,879 and 4,412,073); urethane-modified isocyanurate type urethane isocyanates (see, for instance, Japanese Patent Un-examined Publication (hereunder referred to as "J. P. KOKAI") No. Sho 57-47321 and U.S. Pat. No. 4,582,888). Specific examples of biuret type polyisocyanates are OLESTER NP100 (available from MITSUI TOATSU CHEMICALS, INC.) and Desmodur N-75 (available from Sumitomo Bayer Co., Ltd.); specific examples of HDI isocyanurate type polyisocyanates are Sumidur N-3500 (available from Sumitomo Bayer Co., Ltd.) and CORONATE EH (available from NIPPON POLYURETHANE CO., LTD.). Organic polyisocyanates derived from an aliphatic or alicyclic compound such as isophorone diisocyanate (IPDI) or 4,4'-dicyclohexylmethane diisocyanate are known Specific examples of isocyanurate type polyisocyanates of IPDI include IPDI-T1890 (available from DAICEL-HUELS LTD.); of IPDI urethane-modified polyisocyanates are IPDI-UT647 and IPDI-UT-880 (available from DAICEL-HUELS LTD.). There have been used two-pack urethane coating materials which comprise these hardening agents and acryl polyols or polyester polyols as chief components.

These two-pack urethane coating materials are excellent in various properties such as weatherability, flexibility and wear resistance and secure an immovable position in, for instance, the repair of automobiles and facing of buildings and structures. However, they show insufficient drying characteristics. Therefore, they must be baked at a high temperature or must be allowed to stand for a long time period to obtain well-crosslinked tough coating material films therefrom.

As has been described above, conventional resins for two-pack urethane paints suffer from various drawbacks. For instance, tolylene diisocyanate type resins have high reactivity and hence are excellent in drying characteristics, but show substantially low weatherability, while aliphatic or alicyclic type resins are excellent in weatherability, but have unsatisfactory drying characteristics.

Thus, it has long been desired to develop two-pack urethane coating materials excellent in both weatherability and drying characteristics.

SUMMARY OF THE INVENTION

Accordingly, a first object of the present invention is to provide a novel alicyclic diamine which has a structure quite different from that of $H_6$-XDA and is expected to be a novel starting material for epoxy resins and polyamide resins.

A second object of the present invention is to provide a novel method for preparing the foregoing alicyclic diamine.

The alicyclic diamines according to the present invention are represented by the following general formula (II):

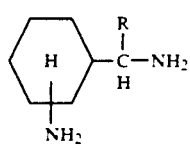

(wherein R represents a hydrogen atom or a lower alkyl group having 1 to 5 carbon atoms and the amino group attached to the cyclohexyl group may be in either of the 2-, 3- and 4-positions) and can be prepared by the method of this invention which comprises catalytically reducing aromatic diamines represented by the following general formula (I):

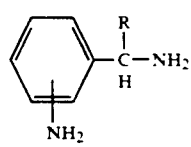

(wherein R is the same as that defined above and the amino group attached to the phenyl group may be in either of the 2-, 3- and 4-positions) in the presence of a ruthenium catalyst, water and an alkali or alkaline earth metal hydroxide.

In this respect, α-(aminocyclohexy)alkylamines represented by the following general formula (II') and α-(3-aminocyclohexyl) ethylamine represented by the following formula (II') are novel compounds

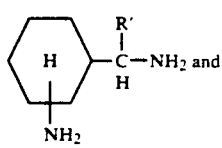

wherein R' represents a lower alkyl group having 2 to 5 carbon atoms and the amino group attached to the cyclohexyl group may be in either of the 2-, 3- and 4-positions.

A third object of the present invention is to provide a novel alicyclic diisocyanate which has a structure quite different from that of $H_6$-XDI and is expected to be a novel starting material for resins such as polyurethane resins and polyurea resins.

A forth object of the present invention is to provide a novel method for preparing the foregoing diisocyanate.

The alicyclic diisocyanate of the present invention is represented by the following general formula (III):

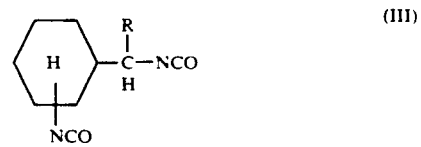

(wherein R represents a hydrogen atom or a lower alkyl group having 1 to 5 carbon atoms and the isocyanato group attached to the cyclohexyl group may be in either of the 2-, 3- and 4-positions) and prepared by the method of this invention comprises reacting alicyclic diamines represented by the following general formula (II):

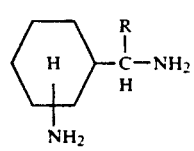

(wherein R is the same as that defined above in connection with the general formula (III) or salts thereof with phosgene.

A fifth object of the present invention is to provide a novel polyisocyanato-isocyanurate which has a structure quite different from that of the resin represented by the formula (c) and is expected to be a novel resin for coating materials and a starting material therefor.

A sixth object of the present invention is to provide a novel method for preparing the foregoing polyisocyanato-isocyanurate.

The polyisocyanato-isocyanurates of the present invention are represented by the following general formula (IV)

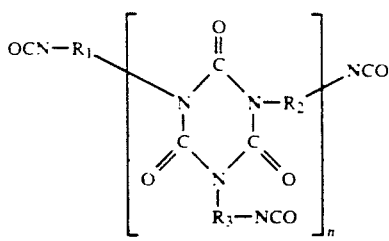

(IV)

wherein $R_1$, $R_2$ and $R_3$ may be the same or different and each represents a group represented by the following general formula:

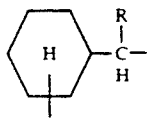

(in the group, R represents a hydrogen atom or a lower alkyl group) and n is an integer ranging from 1 to 5; and prepared by the method of the invention which comprises trimerization of alicyclic diisocyanates represented by Formula (III) in the presence of an alkali metal compound of a carboxylic acid, an alkali metal compound of cyanic acid and optionally a polyethylene oxide compound or an alcohol.

A seventh object of the present invention is to provide an organic polyisocyanate composition which comprises the polyisocyanato-isocyanurate represented by the foregoing formula (IV) in an amount of not less than 10% by weight and less than 100% by weight, and a resin obtained by polymerizing the organic polyisocyanate composition with a compound having at least two active hydrogen atoms as well as a resin composition for coating materials which comprises the aforementioned resin.

DETAILED EXPLANATION OF THE INVENTION

Figure 1:
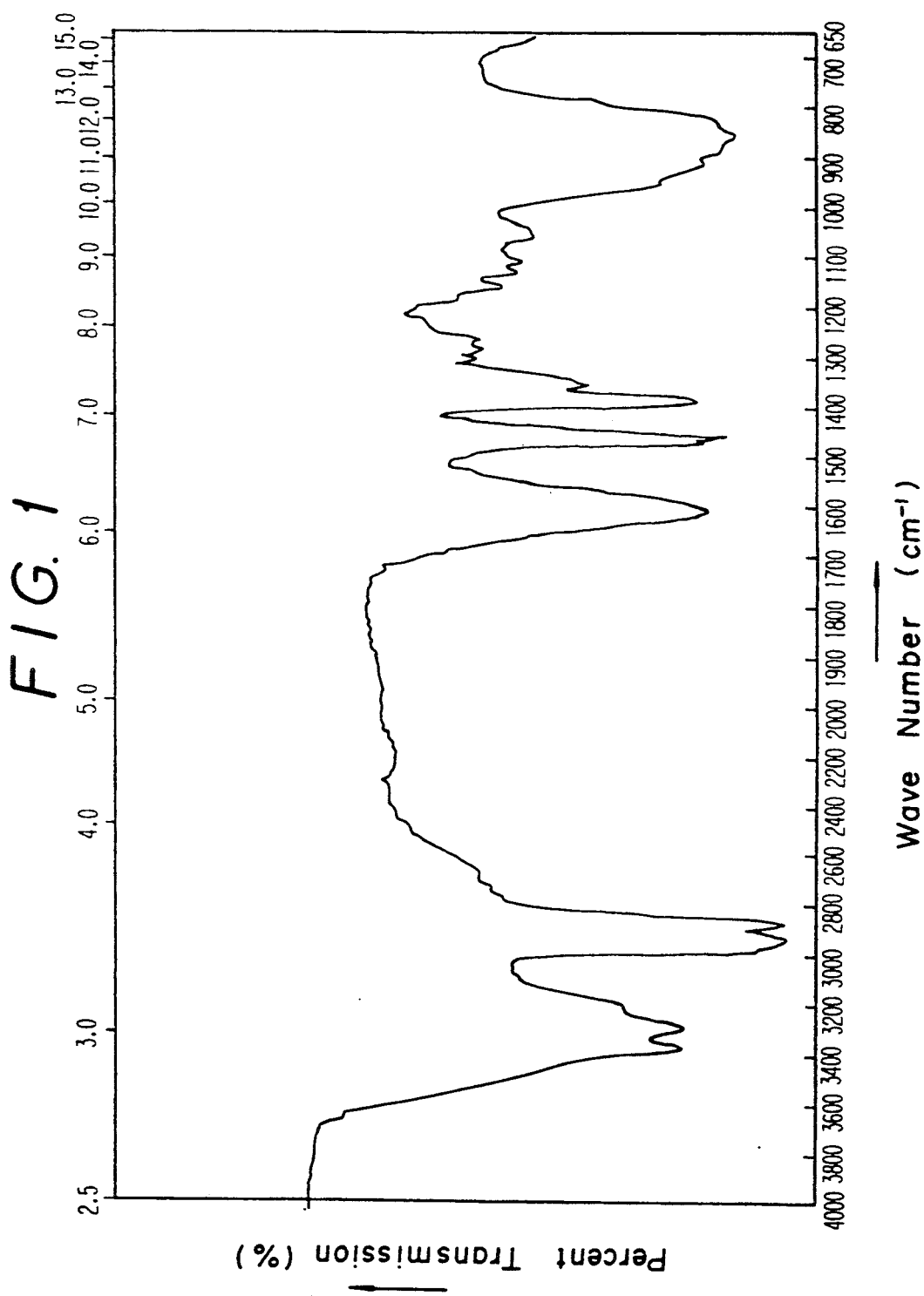
FIG. 1 is an IR chart observed on the α-(3-aminocyclohexyl) ethylamine obtained in Example 1.

The aromatic diamines represented by Formula (I) are novel compounds recently developed and their properties and a method for preparing the same are detailed in Japanese Patent Application Serial Nos. (hereunder referred to as "J.P.A. No(s).") Hei 1-228370 and Hei 1-341120.

A method for preparing the alicyclic diamine represented by Formula (II) according to the present invention will hereinafter be explained in more detail. The alicyclic diamines of the present invention represented by Formula (II) can be prepared by catalytically reducing the foregoing α-(aminophenyl)alkyl-amine represented by Formula (I):

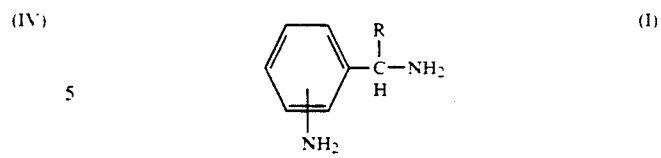

wherein R represents a hydrogen atom or a lower alkyl group having 1 to 5 carbon atoms and the amino group attached to the phenyl group may be in either of the 2-, 3- and 4-positions in the presence of a ruthenium catalyst, water or 1,4-dioxane, and an alkali or alkaline earth metal hydroxide.

The aromatic amines represented by Formula (I) may be industrially effectively prepared by nitrating alkyl phenyl ketone, which is a cheap industrial agent and used as a starting material, to give a nitrophenyl alkyl ketone and then catalytically reducing it in the presence of ammonia; or nitrating an α-aminoalkylbenzene obtained by reductive-amination of an alkyl phenyl ketone and then catalytically reducing the resultant product.

The nitrophenyl alkyl ketone is a nitro compound represented by the following general formula (d):

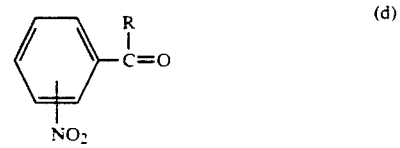

wherein R represents a lower alkyl group having 1 to 5 carbon atoms and the nitro group attached to the phenyl group may be in either of the 2-, 3- and 4-positions and specific examples thereof include nitroacetophenone, nitropropiophenone, nitrophenyl propyl ketone, nitrophenyl butyl ketone and nitrophenyl pentyl ketone.

Specific examples of the α-(aminophenyl)alkylamine compounds represented by the foregoing Formula (I) include α-(2-aminophenyl) ethylamine, α-(3-aminophenyl)ethlamine, α-(4-aminophenyl) ethylamine, α-(2-aminophenyl)propyl-amine, α-(3-aminophenyl) propylamine, α-(4-aminophenyl)-propylamine, α-(2-aminophenyl) butylamine, α-(3-amino-phenyl)butylamine, α-(4-aminophenyl) butylamine, α-(2-aminophenyl)pentylamine, α-(3-aminophenyl) pentylamine, α-(4-aminophenyl)pentylamine, α-(2-aminophenyl) hexylamine, α-(3-aminophenyl)hexylamine and α-(4-aminophenyl) hexylamine.

Specific examples of the α-(aminocyclohexyl)alkylamines represented by Formula (II) prepared according to the method of the present invention are α-(2-aminocyclohexyl)ethylamine, α-(3-aminocyclohexyl)ethylamine, α-(4-aminocyclohexyl)ethylamine, α-(2-aminocyclohexyl)propylamine, α-(3-aminocyclohexyl)propylamine, α-(4-aminocyclohexyl)propylamine, α-(2-aminocyclohexyl)butylamine, α-(3-aminocyclohexyl)butylamine, α-(4-aminocyclohexyl)butylamine, α-(2-aminocyclohexyl)pentylamine, α-(3-aminocyclohexyl)pentylamine, α-(4-aminocyclohexyl)pentylamine, α-(2-aminocyclohexyl)hexylamine, and α-(3-aminocyclohexyl)hexylamine, and α-(4-aminocyclohexyl) hexylamine as well as mixture thereof.

Heretofore, the following methods have been known in order to prepare α-(aminocyclohexyl)alkylamines:

(1) a method which comprises reacting 4-vinyl-1-cyclohexane with ammonia in the presence of a zeolite catalyst to give α-(4-aminocyclohexyl)ethylamine as disclosed in DE No. 3,326,579 (EP No. 132,736) and DE No. 3,327,000 (EP No. 133,938); and (2) a method in which α-(2-aminocyclohexyl)ethylamine is prepared through a pyrazoline obtained from 1-acetyl-cyclohexene and hydrazine as disclosed in DE No. 2,754,553 (U.S. Pat. No. 4,193,905).

However, in the method (1), the reaction is carried out under high temperature (330° C.) and pressure (275 kg/cm²) conditions and the reaction achieves only a low yield in the order of 5.8%. The the method (2) likewise does not achieve satisfactory yield (in the order of 54%). Moreover, the method which comprises reacting 1-acetyl-cyclohexene with hydrazine to cyclize them to thus form 3-methyl-4,5-tetramethylene-2-pyrazoline and then catalytically hydrogenating the product could not provide α-(3-aminocyclohexyl) ethylamine and α-(4-aminocyclohexyl)ethylamine, but provided only 1-methyl-2,3-tetramethylene-1,3-propanediamine, i.e., α-(2-aminocyclohexyl)ethylamine.

The inventors of this invention have conducted various studies to solve the foregoing problems associated with the method for preparing α-(aminocyclohexyl)alkylamines represented by Formula (II).

In other words, the inventors have paid attention to α-(aminocyclohexyl)ethylamine which is the novel diamine disclosed in J.P.A. No. Hei 1-100121, have deeply investigated the method for the preparation thereof, and have found that novel α-(aminocyclohexyl) alkylamines can be prepared by a method comprising catalytically reducing α-(aminophenyl)alkylamines (hereinafter referred to as "APRA") in the presence of a catalyst such as ruthenium.

This compound is in the liquid state at ordinary temperature. In addition, it hardly causes side reactions such as decomposition and deamination during the catalytic reduction. Therefore, it can provide the objective α-(aminocyclohexyl)-alkylamines and mixture thereof in a high yield.

As, in the α-(aminocyclohexyl)alkylamines, one of two amino groups is directly bonded to the cyclohexyl ring and the other is bonded to the secondary carbon atom in the hindered form due to the presence of alkyl groups, the reactivity of these amino groups differs from one another. Thus, these compounds have characteristic properties different from those for alicyclic diamines such as 2,4-diaminocyclohexyl methane, 1,3-bis-(amino-methyl)cyclohexane and 4,4'-diamino-dicyclohexyl methane which have widely been used conventionally.

More specifically, in the conventionally used diamines, all of the two amino groups are directly bonded to the cyclohexane ring or a primary carbon atom and, therefore, the reactivity of these amino groups are almost the same, while the diamines used in the present invention have a substantial difference in the reactivity of the amino groups as already discussed above. In other words, there is an appropriate difference in the reactivity between these two amino groups and thus it is expected that they show characteristic properties as hardening agents for epoxy resins, polyurethanes or polyureas and as starting materials for polyamides.

Moreover, the α-(aminocyclohexyl)alkylamines represented by Formula (I) have asymmetric carbon atoms and, therefore, they are also effective as agents for optical resolution.

Further, as the α-(aminocyclohexyl)alkylamines have a solidifying point of not higher than 0° C. and its vapor pressure is relatively low (in the order of not higher than 0.05 mmHg at 20° C.), they can easily be handled.

The starting materials represented by Formula (I) can be prepared according to the following method. First, the nitro group of the nitro compound represented by Formula (d) is converted into an amino group to thus obtain a compound represented by the following general formula (e):

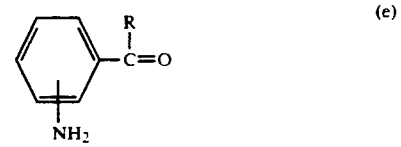

and then the carbonyl group of the compound (e) is further converted into an amino group to obtain the diamine compounds of Formula (I). Alternatively, the nitro compound of Formula (d) may directly be converted into the diamine compounds of Formula (I) through only one stage.

Further, it is also possible to prepare the α-(aminocyclohexyl) alkylamines represented by Formula (I) by reductively aminating alkyl phenyl ketones represented by the following general formula (f) to form α-aminoalkylbenzene represented by the following general formula (g), then nitrating the compound (g) to obtain α-(nitrophenyl)alkylamines represented by the following general formula (h) and finally reducing the nitro group of the compound of Formula (h) to an amino group through hydrogenation:

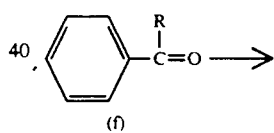

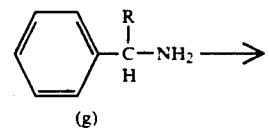

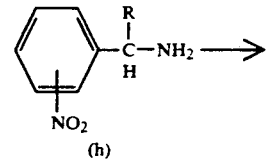

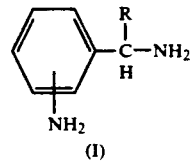

(in formulae (e) to (h) and (I), R is the same as that defined above in connection with Formula (II)).

Now, the one-step method will be described in detail below. A starting material of Formula (d) is dissolved in a solvent such as methanol in an SUS autoclave equipped with a stirring machine, a catalyst such as Raney nickel is added to the solution and the solution is stirred.

Then ammonia is introduced into the solution with cooling at 0° to 10° C. and subsequently hydrogen gas is supplied, under pressure, to about 40 atm. The temperature is raised to about 70° C. and the reaction is performed for about 60 minutes. The reaction is finished when the hydrogen gas absorption is completed.

The reaction solution is distilled in vacuo to give a colorless clear distillate. The distillate is the diamine compound represented by Formula (I).

The catalytic reduction of α-(aminophenyl)alkylamines represented by Formula (I) is performed as follows. First, the foregoing diamine is charged into an SUS autoclave equipped with a stirring machine, then a ruthenium catalyst, water and an alkali or alkaline earth metal hydroxide are added to the diamine and the mixture is heated. Subsequently, hydrogen gas is supplied under pressure up to about 40 atm. and the temperature is raised up to a desired level to perform the catalytic reductive reaction. The reaction is finished when the hydrogen gas absorption is completed. After removal of the catalyst, the reaction solution is distilled in vacuo to obtain a colorless clear distillate. This distillate is the alicyclic diamine compound represented by Formula (II), i.e., α-(aminocyclo-hexyl)alkylamine.

The starting material, α-(aminophenyl)alkylamine, used in the present invention has three isomers whose amino group attached to the phenyl group is present at the 2-, 3- or 4-position. These isomers may be used alone or in combination as the starting materials of the present invention.

The amount of water in the method of this invention preferably ranges from 1 to 40% by weight and more preferably 3 to 20% by weight on the basis of the weight of the α-(amino-phenyl)alkylamine used. This is because, if the amount of water is too great, the amount of by-products having a low boiling point such as α-aminoalkylbenzene and aminoalkylcyclohexane formed tends to increase and sufficient effect of inhibiting side reactions by the addition of an alkaline substance cannot sometimes be achieved. On the other hand, if the amount of water used is too small, the reaction rate is lowered and hence the yield is also reduced.

Water may be used singly, but may also be used in combination with other organic solvents. Such organic solvents which may be used are preferably hydrophilic ones. Specific examples thereof are alcohols such as ethanol, isopropyl alcohol and cyclohexanol.

Examples of the ruthenium catalysts used in the invention include metal ruthenium, ruthenium oxide and ruthenium hydroxide. These catalysts are preferably use in the form supported by a carrier such as carbon, alumina and diatomaceous earth. The amount of these catalysts vary depending on various factors such as the kinds and shapes thereof. For instance, if 5% ruthenium/carbon is employed, it is used in an amount ranging from 0.1 to 10.0% by weight and preferably 0.5 to 2.5% by weight on the basis of the weight of the starting material: α-(aminophenyl)alkylamine.

Specific examples of the alkali or alkaline earth metal hydroxides used in the invention are hydroxides of alkali metals such as lithium, potassium and sodium and alkaline earth metals such as barium, strontium, calcium and magnesium. Alternatively, it is also possible to employ substances which are converted into hydroxides when they come in contact with water such as sodium carbonate and potassium carbonate. However, preferably used are sodium hydroxide and potassium hydroxide from the viewpoint of their price and yield of the objective products.

The amount of these alkali or alkaline earth metal hydroxides preferably ranges from about 0.5 to 16 mole % and more preferably 3 to 10 mole %. If the amount of these alkaline substances is small, it is often observed that the formation of by-products cannot sufficiently be suppressed, while if the alkali substance is used in an amount of more than the upper limit, further improvement in the side-reaction inhibiting effect cannot be achieved.

Hydrogen gas is used in the reaction at a pressure suitably ranging from 20 to 120 kg/cm$^2$, preferably 30 to 80 kg/cm$^2$. The reaction temperature in general ranges from 50° to 220° C., preferably 80° to 150° C. The isoration of the objective product from the reaction mixture can be performed by filtering the mixture, distilling off the water and the reaction solvent and then distilling at a high vacuum.

The method of the present invention makes it possible to reduce α-(aminophenyl)alkylamines to a α-(aminocyclohexyl)-alkylamines in a high yield even under relatively mild conditions at a high reaction rate without a substantial increase in the amount of by-products. Therefore, the present invention is industrially quite advantageous.

The alicyclic diisocyanates represented by Formula (III) are novel compounds which have just been developed recently. A method for the preparation thereof will be explained below.

The alicyclic diisocyanates can be prepared by a method which comprises directly reacting the alicyclic diamines represented by Formula (II) with phosgene or a method which comprises previously preparing a salt of the alicyclic diamine such as hydrochloride and then suspending the salt in an inert solvent to react it with phosgene.

The former process is called "cold-hot two-stage phosgenation". The embodiment of the reaction suffers from no particular restriction. In general, however, gaseous phosgene is introduced into an inert solvent contained in a reactor while cooling the reaction system at a temperature ranging from 0° to 5° C. to dissolve phosgene in the inert solvent almost to its saturated solubility in the solvent, the reactor being equipped with a phosgene gas inlet and a means for sufficiently stirring the reaction system. Then, a solution of the foregoing alicyclic diamine in the same inert solvent is added to the reaction system while introducing gaseous phosgene in an amount 1 to 2 times as much as its stoichiometric quantity. In the mean time, the temperature of the reaction solution is maintained at not higher than 15° C. and the hydrogen chloride generated and excess phosgene are purged out of the reaction system through a reflux condenser. At this stage, the contents of the reactor form a slurry. The main reaction is the formation of carbamyl chloride and amine hydrochlorides. After the addition of the amine solution, the reaction is continued for additional 30 minutes to 2 hours. The procedure described above is referred to as "cold phosgenation".

Then the reaction system is heated to a temperature of 80° C. to 160° C. over 30 minutes to 3 hours. Upon raising the temperature, the phosgene dissolved in the solvent is liable to vaporize and foam and thus it is preferable to reduce the flow rate of phosgene to the order of its stoichiometric quantity, as opposed to the case of the cold phosgenation. After the temperature has been raised, the reaction is continued for additional one to 3 hours. (The procedure described above is called the second-stage reaction in the cold-hot two-stage process). When the slurry is completely dissolved, the reaction is assumed to be completed. The foregoing procedure is called "hot phosgenation". The principal reactions of the hot phosgenation are the decomposition of the carbamyl chloride to isocyanate and the phosgenation of the amine hydrochlorides into isocyanates.

After completion of the hot phosgenation, the reaction system is heated to a temperature of 90° to 170° C. and gaseous nitrogen is blown into the reaction system at a flow rate of not lower than 200 ml/min to remove the dissolved gaseous components and to sufficiently decompose unreacted carbamyl chloride. Then, following cooling, the inert solvent is distilled off under reduced pressure to obtain an alicyclic diisocyanate.

The latter process is referred to as "phosgenation of amine hydrochloride". The hydrochloride of the alicyclic diamine is prepared in advance. The synthesis of the hydrochloride is effected with ease by the well-known method of treating an alicyclic diamine with hydrogen chloride or concentrated hydrochloric acid. The thus-formed alicyclic diamine hydrochloride, which has been fully dried and pulverized, is dispersed in an inert solvent contained in a reactor equipped with means similar to those used in the "cold-hot two-stage phosgenation" process described above. The reaction system is maintained at a temperature ranging from 80° to 160° C., to which system gaseous phosgene is admitted for 3 to 10 hours so that the total phosgene introduction may amount to 2 to 10 times as much as its stoichiometric quantity, to thus obtain an isocyanate. The progress of the reaction may be inferred by the amount of gaseous hydrogen chloride generated, the dissipation of the alicyclic diamine as the starting material which is insoluble in the reaction solvent and hence the transparency and homogeneity of the reaction solution. The hydrogen chloride generated and excess phosgene are discharged through a reflux condenser to the outside of the reaction system. After the reaction has been completed, gaseous nitrogen is introduced into the reaction solvent to remove the dissolved phosgene, and subsequent to cooling and filtration, the inert solvent is distilled out under reduced pressure and further the resulting diisocyanate is purified by distillation under reduced pressure or the like to obtain the objective alicyclic diisocyanate of Formula (III).

It is sufficient to introduce phosgene in an amount 2 to 10 times as much as its stoichiometric quantity for the both prosesses of "cold-hot two-stage phosgenation" and "phosgenation of amine hydrochloride". Examples of the inert solvent which may be used include chlorinated aromatic hydrocarbons such as mono-chlorobenzene and o-dichlorobenzene; and aromatic hydrocarbons such as xylene and toluene; as well as esters such as ethyl acetate, butyl acetate and amyl actate.

The synthesis of the alicyclic diisocyanates of Formula (III) proceeds at an industrially acceptable high velocity in a relatively short reaction time even if the second stage of the cold-hot two stage phosgenation or the phosgenation in the hydrochloride process is performed at a relatively low temperature. This results in the reduction of the amount of the by-products, in particular carbodiimide compounds and the formation of the intended products at high selectivity, and this makes it possible to use a relatively low boiling point without performing the reaction under pressure; to use a variety of inert solvents; to use various kinds of heating mediums required for maintaining the reaction; and to quite easily remove solvents after completion of the reaction.

α-(3-Isocyanato-cyclohexyl)ethylisocyanate represented by the following formula (III') (hereinafter referred to as "IECI") which is one of the novel alicyclic diisocyanates of the present invention shows the following excellent properties compared with conventional diisocyanate compounds.

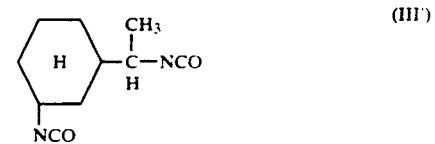

First, as seen from Formula (III'), IECI has an isocyanato group directly bonded to the cyclohexane ring as well as an isocyanato group bonded to the carbon of the alicyclic chain. There is a proper difference in the reactivity with an active hydrogen-containing compound between the both isocycnato groups and for this reason, IECI is expected to have characteristic properties in such a reaction.

Secondary, the urethane resins, urea resins and polyamide resins derived from IECI of the present invention show appropriate mechanical strength and heat resistance since IECI has a substituent at the meta-position of the cyclohexane ring.

Thirdly, IECI of the present invention can be effectively prepared according to a method which will be explained in detail below and in which α-(aminocyclohexyl)ethylamine (hereinafter referred to as "ACEA") or a salt thereof is employed as a starting material even on an industrial scale. Moreover, ACEA can be industrially effectively prepared from acetone which is an industrial reagent of low price.

Fourth, IECI of the present invention is in the liquid state at ordinary temperature and has a low vapor pressure (in the order of 0.002 mmHg at 20° C.). Therefore, it can be relatively easily handled. For instance, the content of isocyanate of α-(isocyanatocyclohexyl)ethylisocyanate is 43.3% (theoretical value) which is high compared with those for the conventional alicyclic or aliphatic diisocyanates.

IECI which is one of the alicyclic diisocyanates show the yellowing resistance and ultraviolet light resistance equal to or higher than those for the conventional alicyclic or aliphatic diisocyanates.

Further, the polyisocyanato-isocyanurates represented by the general formula (IV):

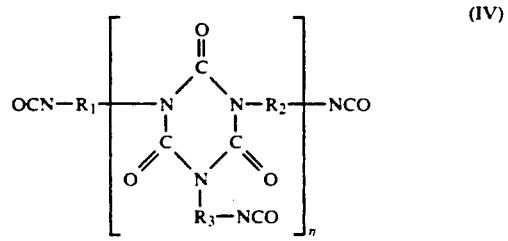

(wherein $R_1$ to $R_3$ may be the same or different and each represents the following group:

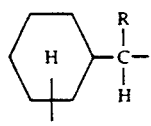

(in the formula, R represents a hydrogen atom or a lower alkyl goup) and n is an integer of 1 to 5) are also novel compounds which have just been developed recently. A method for the preparation thereof will now be explained below.

The polyisocyanato-isocyanurates of Formula (IV) can be prepared by polymerizing isocyanates represented by the above-mentioned general formula (III) in the presence of an alkali metal compound of a carboxylic acid as a trimerizing catalyst, an alkali metal compound of cyanic acid and optionally polyethylene oxide compounds or alcohols.

Specific examples of the isocyanate compounds represented by Formula (III) are α-(2-isocyanatocyclohexyl)ethylisocya-nate, α-(2-isocyanatocyclohexyl)methylisocyanate, α-(2-isocyanatocyclohexyl)propylisocyanate, α-(2-isocyanatocyclo-hexyl)butylisocyanate, α-(2-isocyanatocyclohexyl)pentylisocyanate, α-(3-isocyanatocyclohexyl)ethylisocyanate, α-(3-isocyanatocyclohexyl)methylisocyanate, α-(3-isocyanatocyclohexyl)propylisocyanate, α-(3-isocyanatocyclohexyl)butylisocyanate, α-(3-isocyanatocyclohexyl)pentylisocyanate, α-(4-isocyanatocyclohexyl)ethylisocyanate, α-(4-isocyanatocyclohexyl)methylisocyanate, α-(4-isocyanatocyclo-hexyl)propylisocyanate, α-(4-isocyanatocyclohexyl)butylisocyanate, α-(4-isocyanatocyclohexyl)pentylisocyanate.

Examples of the trimerizing catalysts are organic strong bases such as alkali salts of carboxylic acids, alkali metal ferrite, alkali metal carbonates, tertiary amines, tertiary phosphin, onium compounds of N or P and heterocyclic compounds containing these elements as disclosed in J. H. Saunders et al., Polyurethanes Chemistry and Technology, 1962, 94. In addition, it is also known to use reaction products of Mannich bases or tertiary amines with phosphoric acid, phosphorous acid or alkyl esters of phosphonic acid as disclosed in U.S. Pat. Nos. 4,182,826 and 4,499,253. However, if these alkali metal salts of carboxylic acids, which are known catalysts, are employed alone, the intended trimerization of the compounds of Formula (III) cannot be achieved. Likewise, such trimerization cannot be achieved if the alkali metal salts of cyanic acid are used alone.

The inventors of this invention have found that such a trimerization reaction easily proceeds at a high reaction rate when the alkali metal salts of carboxylic acid and the alkali metal salts of cyanic acid are combined and the combined solid catalyst is used as such, compared with the reaction rates observed when they are separately used in the reaction.

Good results have been obtained when the catalyst is added according to the following method. First the diisocyanate compound of Formula (III) is admixed with a polyethylene oxide compound (for instance, polyethylene glycol having a molecular weight ranging from 200 to 1,000 and polyethylene glycol monomethyl ether) or alcohols and then a combined catalyst comprising the alkali metal salt of carboxylic acid and the alkali metal salt of cyanic acid is added thereto.

The best result can be achieved when the combined catalyst is added in the form of a solution in the polyethylene oxide compound or the alcohols. More specifically, it has been found that the trimerization can be markedly accelerated and the maintenance of the reaction becomes substantially easy if the catalyst is used in such a manner.

Specific examples of the metal salts of carboxylic acids used as the trimerization catalysts are salts of alkali metal and other metals such as tin, zinc and lead with alkyl carboxylic acids such as acetic acid, propionic acid, butyric acid, valeric acid, caproic acid and octylic acid. Preferred is potassium acetate. Specific examples of the alkali metal salts of cyanic acid are alkali metal cyanates such as sodium cyanate, potassium cyanate and lithium cyanate; and cyanates of other metals such as tin, zinc, lead, silver and gold. Preferred is potassium cyanate among others.

Specific examples of the polyethylene oxide compounds are polyethylene glycols having a molecular weight ranging from 200 to 1,000, polyethylene glycol monomethyl ether and polyethylene glycol dimethyl ether and preferred is polyethylene glycol having a molecular weight of 400.

Specific examples of the alcohols which can be used in the present invention are methanol, ethanol, butanol, ethylene glycol, 1,3-butanediol, neopentyl glycol, 2-ethyl-1,3-hexanediol, trimethylolpropane, polypropylene glycol and phenol.

Regarding the amount of the catalyst, it has been found that the trimerization can markedly be accelerated if the alkali metal salt of cyanic acid is used in an amount ranging from 0.05 to 20 moles and the polyethylene oxide compound or an alcohol is used in an amount ranging from 1 to 50 moles per mole of the metal salt of carboxylic acid.

As the reaction solvents, there may be used in the present invention organic solvents usually employed in the preparation of isocyanates. Specific examples of solvents preferably used in the invention are esters such as ethyl acetate and butyl acetate; ketones such as acetone and methyl ethyl ketone; aromatic substances such as benzene, toluene and xylene; and aprotic solvents such as dimethylsulfoxide, tetramethylsulfone, tetrahydrofuran, N-methylpyrrolidone, N,N-dimethylformamide, N,N'-tetramethyl urea and 1,3-dimethylimidazolidinone.

When a solvent is used, or even when it is not used, a solution comprising the foregoing potassium acetate, potassium cyanate, polyethylene glycol having a molecular weight of 400, and optionally a solvent, is previously prepared and is added to the reaction system.

The reaction time can be adjusted by appropriately selecting the amount of the catalyst and the reaction temperature.

The temperature of the trimerization ranges from 0° to 150° C., preferably 30° to 80° C.

Moreover, as a reaction stopping agent, there may be used, for instance, acids such as sulfuric acid, orthophosphoric acid, polyphosphoric acid, p-toluenesulfonic acid, acetic acid, trifluoroacetic acid and benzenesulfonic acid; and acid chlorides such as benzoyl chloride and acetyl chloride.

The coloring observed during the trimerization reaction can effectively be prevented by the addition of an antioxidant as a stabilizer to the reaction system prior to the initiation of the reaction.

As such reaction stabilizers or storage stabilizers, organic phosphoric acid compounds and phenolic compounds can be used. Specific examples thereof are 2,6-di-tert-butyl-4-methylphenol, triphenyl phosphite, triethyl phosphite and diisodecylpentaerythritol diphosphite.

Specific examples of the compounds of Formula (IV) in which n is 1 include N,N',N''-tris(2-(α-isocyanatoethyl)cyclohexyl) isocyanurate, N,N',N''-tris(2-isocyanato-α-ethylcyclohexyl) isocyanurate, N,N',N''-tris(2-isocyanato-cyclohexylmethyl)isocyanurate, N,N',N''-tris(2-(α-isocyanatopropyl)cyclohexyl) isocyanurate, N,N',N''-tris(2-isocyanato-α-cyclohexyl-propyl) isocyanurate, N,N',N''-tris(2-(α-isocyanatobutyl)cyclohexyl) isocyanurate, N,N',N''-tris(2-isocyanato-α-cyclo-hexylbutyl) isocyanurate, N,N',N''-tris(2-(α-isocyanato-pentyl)cyclohexyl) isocyanurate, N,N',N''-tris(2-isocyanato-α-cyclohexylpentyl) isocyanurate, N,N',N''-tris(3-(α-isocyanato-ethyl)cyclohexyl) isocyanurate, N,N',N''-tris(3-isocyanato-α-ethylcyclohexyl) isocyanurate, N,N',N''-tris(3-isocyanato-cyclohexylmethyl) isocyanurate, N,N',N''-tris(3-(α-isocyanatopropyl)cyclohexyl) isocyanurate, N,N',N''-tris(3-isocyanato-α-cyclohexylpropyl) isocyanurate, N,N',N''-tris(3-(α-isocyanatobutyl)cyclohexyl) isocyanurate, N,N',N''-tris(3-isocyanato-α-cyclohexylbutyl) isocyanurate, N,N',N''-tris(3-(α-isocyanatopentyl)cyclohexyl) isocyanurate, N,N',N''-tris(3-isocyanato-α-cyclohexylpentyl) isocyanurate, N,N',N''-tris(4-(α-isocyanatoethyl)cyclohexyl) isocyanurate, N,N',N''-tris(4-isocyanato-α-cyclohexylethyl) isocyanurate, N,N',N''-tris(4-isocyanatomethyl)-cyclohexyl) isocyanurate, N,N',N''-tris(4-isocyanato-cyclohexylmethyl) isocyanurate, N,N',N''-tris(4-(α-isocyanatopropyl)cyclohexyl iso-cyanurate, N,N',N''-tris(4-isocyanato-α-cyclohexylpropyl) isocyanurate, N,N',N''-tris(4-(α-isocyanatobutyl)cyclohexyl) isocyanurate, N,N',N''-tris(4-isocyanato-α-cyclohexylbutyl) isocyanurate, N,N',N''-tris(4-(α-isocyanatopentyl)cyclohexyl) isocyanurate, N,N',N''-tris(4-isocyanato-α-cyclohexylpentyl) isocyanurate, N,N'-bis(2-(α-isocyanatoethyl)cyclohexyl)-N''-(2-(α-isocyanatopropyl)cyclohexyl)-isocyanurate, N,N'-bis(2-isocyanato-α-cyclohexylethyl)-N''-(2-(isocyanato-α-cyclohexylpropyl)isocyanurate, N,N'-bis(2-isocyanato-methyl)cyclohexyl)-N''-(2-(α-isocyanatoethyl) cyclohexy)isocyanurate, N,N'-bis(2-isocyanato-cyclohexylmethyl)-N''-(2-isocyanato-α-cyclohexylethyl)isocyanurate, N,N'-bis(3-(α-isocyanatoethyl)cyclohexyl)-N''-(3-(α-isocyanato-propyl)cyclohexyl)isocyanurate, N,N'-bis(3-isocyanato-α-cyclohexyl-ethyl)-N''-(3-(isocyanato-α-cyclohexylpropyl)isocyanurate, N,N'-bis(3-isocyanatomethyl)cyclohexyl)-N''41 -(3-(α-isocyanato-ethyl)cyclohexy) isocyanurate,N,N'-bis(3-isocyanato-cyclo-hexylmethyl)-N''-(3-isocyanato-α-cyclohexyl-ethyl)isocyanurate, N,N'-bis(4-(α-isocyanato-ethyl)cyclohexyl)-N''-(4-(α-isocyanato-propyl)cyclohexyl)isocyanurate, N,N'-bis(4-isocyanato-α-cyclohexylethyl)-N''-(4-(isocyanato-α-cyclohexylpropyl)isocyanurate, N,N'-bis(4-isocyanatomethyl)cyclohexyl)-N''-(4-(α-isocyanato-ethyl)cyclohexy)iso-cyanurate, N,N'-bis(4-isocyanato-cyclohexylmethyl)-N''-(4-isocyanato-α-cyclohexylethyl) isocyanurate, N,N'-bis(4-α-isocyanatoethyl)cyclohexyl)-N''-(3-(α-isocyanatoethyl)cyclohexyl) isocyanurate, N,N'-bis(4-isocyanato-α-cyclohexylethyl)isocyanurate-N''-(3-isocyanato-α-cyclohexylethyl) isocyanurate, N,N'-bis(4-isocyanatomethyl)-cyclohexyl)-N''-(3-(isocyanatomethyl)cyclohexyl)isocyanurate, N,N'-bis(4-isocyanato-cyclohexyl-methyl)-N''-(3-isocyanato-cyclohexyl-methyl)isocyanurate, N,N'-bis(4-(α-isocyanatopropyl)-cyclohexyl)-N''-(3-(α-isocyanato-propyl) cyclohexyl)isocyanurate, N,N'-bis(4-isocyanato-α-cyclohexyl-propyl)-N''-(3-isocyanato-α-cyclohexyl-ethyl) isocyanurate, N,N'-bis(4-isocyanatomethyl)-cyclohexyl)-N''-(2-isocyanato-methyl)-cyclohexyl)isocyanurate, N,N'-bis(4-isocyanatocyclohexyl)-N''-(2-isocyanato-cyclohexyl-methyl)isocyanurate.

N,N'-bis(4-(α-isocyanatopropyl)cyclohexyl)-N''-(2-(α-isocyanatopropyl)cyclohexyl)isocyanurate, N,N'-bis(4-isocyanato-α-cyclohexyl-propyl)-N''-(2-isocyanato-α-cyclohexyl-propyl) isocyanurate, N,N'-bis(3-(α-isocyanato-ethyl)cyclohexyl)-N''-(2-(α-isocyanato-ethyl)cyclohexyl) isocyanurate, N,N'-bis(3-isocyanato-α-cyclohexyl-ethyl)-isocyanurate-N''-(2-isocyanato-α-cyclohexyl-ethyl)isocyanurate, N,N'-bis(3-isocyanatomethyl)cyclohexyl)-N''-(2-(isocyanatomethyl)-cyclohexyl) isocyanurate. N,N'-bis(3-isocyanato-cyclohexyl-methyl)-N''-(2-isocyanatocyclohexylmethyl)isocyanurate, N,N'-bis(3-(α-isocyanato-propyl) cyclohexyl)-N''-(2-(α-isocyanato-propyl) cyclohexyl)isocyanurate, N,N'-bis(3-isocyanato-α-cyclohexyl-propyl)-N''-(2-(isocyanato-α-cyclohexyl-propyl)isocyanurate, N,N'-bis(3-(α-isocyanato-ethyl)cyclohexyl)-N''-(4-(α-isocyanato-ethyl) cyclohexyl) isocyanurate, N,N'-bis(3-isocyanato-α-cyclohexyl)isocyanurate-N''-(4-isocyanato-α-cyclohexyl-ethyl)isocyanurate, N,N'-bis(3-isocyanatomethyl)-cyclohexyl)-N''-(4-(isocyanato-methyl)-cyclohexyl) isocyanurate, N,N'-bis(3-isocyanato-cyclohexyl-methyl)-N''-(4-isocyanato-cyclohexylmethyl)isocyanurate, N,N'-bis(3-(α-isocyanatopropyl) cyclohexyl)-N''-(4-(α-isocyanatopropyl) cyclohexyl) isocyanurate, N,N'-bis(3-isocyanato-α-cyclohexyl-propyl)-N''-(4-(isocyanato-α-cyclohexylpropyl)isocyanurate, N,N'-bis(2-(α-isocyanato-ethyl)cyclohexyl-N''-(3-(α-isocyanato-ethyl)-cyclohexyl) isocyanurate, N,N'-bis-(2-isocyanato-α-cyclohexylethyl)-N''-(3-isocyanato-α-cyclohexylethyl)isocyanurate, N,N'-bis(2-isocyanatomethyl)-cyclohexyl)-N''-(3-(isocyanatomethyl)cyclohexyl)isocyanurate, N,N'-bis(2-isocyanato-cyclohexylmethyl)-N''-(3-isocyanato-cyclohexylmethyl)isocyanurate, N,N'-bis(2-(α-isocyanato-propyl)cyclohexyl)-N''-(3-(α-isocyanatopropyl)cyclohexyl)isocyanurate, N,N'-bis(2-isocyanato-α-cyclohexylpropyl)-N''-(3-(isocyanato-α-cyclohexylpropyl)isocyanurate, N,N'-bis(2-(α-isocyanatoethyl)cyclohexyl)-N''-(4-(α-isocyanato-ethyl)cyclohexyl)isocyanurate, N,N'-bis-(2-isocyanato-α-cyclohexyl-ethyl)-isocyanurae-N''-(4-isocyanato-α-cyclohexylethyl)isocyanurate, N,N'-bis(2-isocyanatomethyl)cyclohexyl)-N''-(4-(isocyanato-methyl)-cyclohexyl)isocyanurate, N,N'-bis(2-isocyanato-cyclohexyl-methyl)-N''-(4-isocyanato-cyclohexyl-methyl) isocyanurate, N,N'-bis(2-(α-isocyanatopropyl)cyclohexyl)-N''-(4-(α-isocyanatopropyl)cyclohexyl)isocyanurate, N,N'-bis(2-isocyanato-α-cyclohexyl-propyl)-N''-(4-(isocyanato-α-cyclohexyl-propyl) isocyanurate, N-(3-(α-isocyanatoethyl)cyclohexyl)-N', N''-bis(3-(α-isocyanatopropyl)- cyclohexyl)isocyanurate, N-(3-isocyanato-α-cyclohexyl-ethyl)-N',N"-bis(3-isocyanato-α-cyclohexyl-propyl) isocyanurate, N-(3-isocyanato-methyl)cyclohexyl)-N',N"-bis(3-α-isocyanato-ethyl)-cyclohexyl) isocyanurate, N-(3-isocyanato-cyclohexyl-methyl)-N',N"-bis(3-isocyanato-α-cyclohexyl-ethyl) isocyanurate, N-(2-(isocyanatoethyl)cyclohexyl)-N',N"-bis(2-(α-isocyanatopropyl)cyclohexyl)isocyanurate, N-(2-isocyanato-cyclohecylethyl)-N',N"-bis (2-isocyanato-cyclohexyl-propyl)isocyanurate, N-(2-(isocyanatomethyl)cyclohexyl)-N',N"-bis(2-(α-isocyanato-ethyl) cyclohexyl)isocyanurate, N-(2-iso-cyanato-cyclohexylmethyl)-N',N"-bis(2-isocyanato-α-cyclohexylethyl)-isocyanurate, N-(4-isocyanato-methyl) cyclohexyl-N,',N"'-bis(4-(α-isocyanato-ethyl)cyclohexyl) isocyanurate, N-(4-isocyanato-cyclohexyl-methyl)-N',N"-bis(4-isocyanato-α-cyclohexylethyl)isocyanurate, N-(4-α-isocyanato-ethyl) cyclohexyl-N', N"-bis(4-(α-isocyanatopropyl)cyclohexyl)isocyanurate and N-(4-isocyanato-α-cyclohexyl-ethyl)-N',N"-bis(4-(isocyanato-α-cyclohexylpropyl)isocyanurate.

Moreover, examples of the compounds of Formula (IV) in which n is 2, 3, 4 or 5, are oligonmers corresponding to those listed above.

Preferred embodiments of the method for preparing the objective compounds of Formula (IV) will now be explained below.

First, a solvent for dissolving the objective compound (IV) is selected and prepared. Examples of such solvents are butyl acetate, ethyl acetate, cellosolve acetate, acetone, methy ethyl ketone, benzene, toluene and xylol.

The amount of the solvent selected ranges from 5 to 150 parts by weight per 100 parts by weight of the compound of Formula (III). In this respect, the compound of Formula (III) may be used alone or in combination in a proper ratio. The preparation thus obtained is referred to as principal starting material A. It is herein noted that if the compound is used in an amount of less than 5% by weight, the objective product can be obtained, but its yield achieved is not industrially acceptable.

Separately, a mixture containing a catalyst or the like (hereinafter referred to as "catalyst B") and a mixture containing a reaction stopping agent (hereinafter referred to as "reaction stopping agent C") are prepared.

More specifically, the catalyst B is obtained by dissolving, in the solvent used for preparing the principal material A, an alkali metal salt of carboxylic acid, and alkali metal salt of cyanic acid and a polyethylene oxide compound or an alcohol as the trimerization catalyst and a stabilizer. Regarding the mixing ratio, the alkali metal salt of carboxylic acid is used in an amount ranging from 1 to 10% by weight on the basis of the weight of the solvent; the amount of the alkali metal salt of cyanic acid ranges from 0.05 to 20.0 moles and preferably 0.2 to 0.8 mole; that of the polyethylene oxide compound or the alcohol ranges from 1.0 to 50 moles and that of the stabilizer ranges from 0.01 to 0.5 mole, preferably 0.05 to 0.1 mole, per mole of rhe alkali metal salt of carboxylic acid. The amount of the alkali metal salt of carboxylic acid ranges from 0.0001 to 0.1 mole, preferably 0.001 to 0.01 mole per mole of the solute (diisocyanate) of the principal material A.

The stabilizer also serves to inhibit the coloring and the change of properties of the objective products during reaction and storing.

The reaction stopping agent C can be prepared by dissolving the reaction stopping agent in the solvent used for preparing the principal material A. The amount thereof dissolved in the solvent ranges from 0.5 to 5% by weight on the basis of the weight of the solvent. The reaction stopping agent is used in an amount ranging from 0.001 to 0.5% by weight, preferably 0.01 to 0.3% by weight on the basis of the total weight of the solute (diisocyanate) of the principal material A.

A reaction vessel which is equipped with a stirring machine, a thermometer, a dropping funnel, a reflux condenser and a pipe for introducing an inert gas is used in the reaction by taking into consideration that this reaction system undergoes a liquid-liquid mixing reaction. The reaction vessel is preferably provided with a means for controlling the temperature of the reaction system such as those capable of heating, heat retaining or cooling the system.

A desired amount of the principal material A is introduced into the reaction vessel or a diisocyanate of Formula (II) and a solvent are introduced into the vessel and the diisocyanate is dissolved in the solvent at a room temperature to prepare the principal material A and the reaction system is stirred while being blanketed with an inert gas such as nitrogen or argon gas, wherein the temperature is maintained at 20° to 30° C.

The catalyst B is dropwise added to the solution, the temperature is raised to T° C. and the reaction is continued for 1.0 to 15 hours. In this case, the temperature T ranges from 0° to 150° C., preferably 30° to 80° C. If the temperature is lower than 0° C., the objective polyisocyanato-isocyanurate can be obtained, but the yield and/or the reaction rate are not industrially acceptable, while if it is higher than 150° C., the polyisocyanato-esocyanurate can of course be obtained. However, the yield of the product of Formula (I) wherein n is 1 decreases, while not only that for each product of Formula (I) in which n is 2, 3, 4 or 5 is increased, but also the product having n of 6 or higher is increased.

The progress of the reaction can be monitored by determining the amount of NCO present in the reaction system; or by measuring the quantity of unreacted monomers in terms of gas chromatography. In general, if the conversion reaction excessively proceeds, the viscosity of the product increases and the compatibility with the polyol is lowered. Therefore, generally the degree of conversion is controlled to a low level to thus remain unreacted raw materials in the reaction system and the unreacted materials are removed after stopping the reaction.

When the reaction proceeds to a desired degree of conversion, a deactivator for the catalyst such as phosphoric acid is added and then the temperature of the reaction system is returned to room temperature with stirring. The unreacted monomers and the solvent are removed by, for instance, a continuous distillation technique or solvent-extraction technique.

The analysis and identification of the resulting products are performed as follows:

The methylcarbamate compound which has been obtained by reacting the reaction product with methyl alcohol is subjected to gel permeation chromatography (GPC) measurement. The molecular weight distribution of the compound is determined by the compositional analysis thereof in terms of HSLC by the GPC column.

The inventors of this invention have conducted various studies to solve the problems associated with the conventional two-pack urethane coating materials, have found that the resins for two-pack urethane coating materials which comprise the polyisocyanato-isocyanurate represented by Formula (IV) and a polyol compound are excellent in drying properties and weatherability and thus have completed the present invention.

Consequently, the present invention relates to a resin composition for two-pack urethane coating materials which comprises an organic polyisocyanate containing 10 to 100% by weight of the polyisocyanato-isocyanurate of Formula (IV) and a compound having at least two active hydrogen atoms in the molecule.

In the foregoing resin composition, the equivalent ratio of the organic polyisocyanate to the compound having active hydrogen atoms ranges from 0.1:1 to 10:1, preferably 0.5 to 2.0 and more preferably 0.8 to 1.2.

The organic polyisocyanate containing 10 to 100% by weight of the polyisocyanato-isocyanurate of Formula (IV) which is used in the resin composition for two-pack urethane coating materials according to the present invention herein means a polyisocyanate obtained through the foregoing trimerization reaction, or a mixture thereof with a modified product of an aliphatic or alicyclic compound such as hexamethylene diisocyanate, isophorone diisocyanate or 4,4'-dicyclohexylmethane diisocyanate obtained through the reaction with urethane and/or biuret.

In this mixture, if the amount of the polyisocyanatoesocyanurate represented by Formula (IV) is less than 10% by weight, it is difficult to obtain resins for two-pack urethane coating materials having good drying properties.

Examples of the compounds having at least two active hydrogen atoms used in the invention are glycols, alkane polyols, polyether polyols, polyester polyol resins, acryl polyol resins, epoxy resins or monomers or polymers of aromatic or heterocyclic polyhydric alcohols.

Specific examples thereof include glycols such as ethylene glycol, propylene glycol, beta, beta'-dihydroxydiethyl ether (diethylene glycol), dipropylene glycol, 1,4-butylene glycol, 1,3-butylene glycol 1,6-hexamethylene glycol, neopentyl glycol, polyethylene glycol, polypropylene glycol, polypropylene-poly-ethylene glycol and polybutylene glycol; alkane polyols such as glycerin, trimethylolpropane, hexanetriol, pentaerythritol, xylitol and sorbitol; polyether polyols obtained by adding an alkylene oxide or mixture thereof (for instance, ethylene oxide, propylene oxide and 1,2-butylene oxide) to a polyhydric alcohol or mixture thereof such as glycerin or propylene glycol; polyether polyols such as those obtained by reacting alkylene oxide with polyfunctional compounds such as ethylenediamine or ethanolamine; polyester polyol resins such as those obtained by condensing a polyhydric alcohol or mixture thereof selected from the group consisting of, for instance, ethylene glycol, propylene glycol, diethylene glycol, dipropylene glycol, 1,4-butylene glycol 1,3-butylene glycol, 1,6-hexamethylene glycol, neopentyl glycol, glycerin and trimethylolpropane with a dibasic acid or mixture thereof selected from the group consisting of succinic acid, adipic acid, sebacic acid, dimer acids, maleic anhydride, phthalic anhydride, isophthalic acid and terephthalic acid; acryl polyols obtained by, for instance, copolymerizing polymerizable monomer having at least one active hydrogen in the molecule with copolymerizable other monomers; acryl polyol resins such as those obtained by polymerizing acryl esters having active hydrogen atoms (for instance, 2-hydroxyethyl acrylate, 2-hydroxypropyl acrylate and 2-hydroxybutyl acrylate), methacrylates having active hydrogen atoms (for instance, 2-hydroxyethyl methancrylate, 2-hydroxypropyl methacrylate and 2-hydroxybutyl methacrylate), acrylic acid monoester or methacrylic acid monoester of glycerin, acrylic acid monoester or methacrylic acid monoester of trimethylolpropane or mixture thereof; with acrylic acid esters (for instance, methyl acrylate, ethyl acrylate, isopropyl acrylate, n-butyl acrylate and 2-ethylhexyl acrylate), methacrylic acid esters (for instance, methyl methacrylate, ethyl methacrylate, isopropyl methacrylate, n-butyl methacrylate, isobutyl methacrylate, n-hexyl methacrylate and lauryl meth-acrylate) or mixture thereof; in the presence of or absence of unsaturated carboxylic acids (for instance, acrylic acid, methacrylic acid, maleic acid and itaconic acid), unsaturated amides (for instance, acrylamide, N-methylol acrylamide and diacetone acrylamide), or other polymerizable monomers (for instance, glycidyl methacrylic acid, styrene, vinyl toluene, vinyl acetate and acrylonitrile) or mixture thereof; and epoxy resins such as those novolak type, β-methylepichlo type, cyclic oxirane type, glycidyl ether type, glycidyl ester type, glycol ether type, epoxylated aliphatic unsaturated compound type, epoxylated aliphatic ester type, polycarboxylic acid ester type, aminoglycidyl type, halogenated type and resorcin type ones. Monosaccharides such as fruit sugar, grape sugar, cane sugar, milk sugar, 2-methyl glycoside and derivatives thereof; and aromatic or heterocyclic polyhydric alcohols such as trimethylolbenzene and tris(2-hydroxyethyl)esocyanurate are also included in addition to the foregoing compounds. These compounds may be used alone or in combination or further in combination with at least one member selected from the group consisting of other compounds having at least two active hydrogen atoms such as primary or secondary amino group-containing compounds (for instance, ethylenediamine, triethylenediamine, hexamethylenediamine, m-xylylenediamine, diaminodiphenylmethane, isophorone-diamine, diethylenetriamine, polyamines such as those obtained by adding various alkylene polyamines to alkylene oxides and N,N'-dimethylethylenediamine), substituted urea compounds (for instance, N,N'-dimethyl urea and N-methyl-N'-cyclohexyl urea), mercapto group-containing compounds (for instance, 1,2-ethane-dithiol, 1,6-hexanedithiol, polyether polythiol and polyester polythiol), carboxyl group-containing compounds (for instance, succinic acid, adipic acid, sebacic acid, terephthalic acid and polybutadiene having carboxyl termini), or compounds having different groups containing active hydrogen atoms in the molecule (for instance, monoethanolamine, thioethanolamine, lactic acid and β-alanine).

Although various compounds having active hydrogen atoms have been exemplified above specifically, the present invention is not restricted to the compounds specifically listed above and any compounds having active hydrogen atoms may be employed so far as they can react with polyisocyanates used in making resin compositions for two-pack urethane coating materials according to the present invention and any combination of these compounds may be employed.

When the both components of the resin compositions for two-pack urethane coating materials according to the present invention are mixed together, appropriate solvents may optionally be used. Such a solvent is properly selected, depending on the purposes and applications, from the group consisting of, for instance, hydrocarbons (for instance, benzene, toluene, xylene, cyclohexane, mineral spirits and naphtha), ketones (for instance, acetone, methyl ethyl ketone methyl isobutyl ketone) and esters (for instance, ethyl acetate, n-butyl acetate, cellosolve acetate and isobutyl acetate). These solvents may be used alone or in combination.

The resin compositions of the present invention may further comprise other additives commonly employed in this field, depending on the purposes and applications, such as catalysts, pigments, leveling agents, antioxidants, plasticizers and surfactants.

Specific examples of such catalysts used in the invention are triethylamine, triethylenediamine, stannous octoate, dibutyl tin di-2-ethylhexoate, lead 2-ethylenehexoate (Pb 24%), sodium O-phenylphenate, potassium oleate, bismuth nitrate, tetra-(2-ethyl-hexyl) titanate, stannic chloride, ferric chloride, ferric 2-ethylhexoate (Fe 6%), cobalt 2-ethylhexoate (Co 10%), zinc naphthenate (Zn 14.5%), antimony trichloride, N-methylmorpholine, N,N-dimethylbenzylamine, N-ethylmorpholine, N,N-dimethyllauryl-amine, N,N-dimethylpiperazine, N,N,N',N'-tetramethylethylenediamine, N,N,N',N'-tetramethylpropyldiamine, N,N,N',N'-tetramethyl-1,3-butanediamine, hexamethylenetetramine, cobalt naphthenate, tetra-n-butyl tin, tri-n-butyl tin acetate and dibutyl tin dilaurate.

Specific examples of the pigments usable in the invention include potassium titanate fibers (available from Ohtsuka Kagaku), aluminum oxide (for instance, Emery available from SUMITOMO METAL MINING CO., LTD.), silica, titanium oxide, Fillite (available from Nippon Fillite Co., Ltd.), metal powders (such as copper and copper alloy powders, iron and iron alloy powders, nickel and nickel alloy powders, and zinc, tin, lead, aluminum and magnesium powders), mica and Suzorite mica (available from U.S. Marietta Resources International Inc.). In addition, as anticorrosive paints there may be mentioned, for instance, zinc chromate (available from Nihon Muki Kagaku Kogyo kk), Molywhite (available from Nihon Shawin-Williams Chemical k.k.) and titanium dioxide (available from TEIKOKU KAKO CO., LTD.).

Specific examples of the leveling agents usable in the present invention are organic modified polysiloxanes (available from Parker Corporation under the trade name of EFKA TM -30, 31, 34, 35) and specific examples of the antioxidants are Addital XL 109 and 297 (available from Hoechst Co., Ltd.).

The resin composition for two-pack urethane coating materials according to the present invention is used by mixing, immediately before forming a polyurethane resin, the aforesaid organic polyisocyanate and active hydrogen-containing compound as well as solvents and/or other additives selected depending on the purposes and applications and the composition may be used at a temperature ranging from room temperature to 150° C.

The composition of the present invention as a two-pack coating material shows excellent adhesion to materials to be coated therewith such as metals, plastics, rubbers, leathers and concrete and thus can widely be employed in a variety of fields such as vehicles, equipments and installations, construction materials and woodworking products.

In general, polyurethane coating materials have adhesion to materials to be coated therewith, hardness and flexibility which are well-balanced with each other and are excellent in resistance to cracking, water resistance, resistance to chemicals, luster and appearance. On the other hand, the polyurethane coating obtained by applying the composition of the present invention as a coating material shows excellent weatherability and photostability in addition to the foregoing properties. Further, the coated film provides the following excellent characteristics compared with commerically available coating materials. First, the isocyanurate type polyisocyanate used in the composition of the invention has high initial curing and drying properties compared with aliphatic polyisocyanates such as organic polyisocyanates derived from hexamethylene diisocyanate and is excellent in compatibility. Therefore, the coated film has very excellent appearance and coated film performance thereof are comparable to or higher than those for coated films derived from commercially available coating materials. Thus, they are favorable for use in applications such as coating of vehicles in which workability, appearance and coated film performance are regarded as of major importance.

The present invention will hereinafter be explained in more detail with reference to the following Examples, but the invention is not restricted to these specific Examples.

EXAMPLE 1

Preparation of α-(3-aminocyclohexyl)ethylamine

To a 400 ml inner volume SUS 316L autoclave equipped with a stirring machine, there were added 50.2 g (0.369 mole) of α-(3-aminophenyl)ethylamine (APEA), 12.1 g of water, 1.20 g (solid content) of 5% ruthenium/carbon catalyst and 1.2 g (0.03 mole) of flake-like sodium hydroxide, the internal atmosphere was replaced with nitrogen gas and the content of the autoclave was stirred for a while. Then, hydrogen gas was introduced into the autoclave under pressure to a pressure of 40 kg/cm$^2$G and thereafter the temperature was raised up to 110° C. Hydrogen gas was further introduced thereinto under pressure to a pressure of 80 kg/cm$^2$G, but it was absorbed as the reaction proceeded and correspondingly its pressure was reduced. Thus, the reaction was continued while hydrogen gas was intermittently introduced so that the pressure thereof was maintained at a level ranging from 60 to 80 kg/cm$^2$G. During the reaction, the temperature was adjusted to 110° C. The absorption of hydrogen gas did not take place any more at the time when the total amount of hydrogen gas absorbed reached about 24.8N l (corresponding to the stoichiometric amount) and, therefore, the reaction was stopped. The reaction mixture was cooled to room temperature, it was removed and filtered. After removing water from the filtrate by distillation in vacuo, distillation was further carried out at a pressure of 3 to 6 mmHg to obtain 42.5 g (yield 81.1%) of a distillate having a distillation range of 83° to 93° C.

The resulting liquid was colorless and clear and was identified to be α-(3-aminocyclohexyl)ethylamine in terms of elemental analysis, GC-MC spectra, IR spectra, $^1$H-NMR spectra. The results thus observed are listed below or shown in the attached Figs. In addition, the purity thereof as determined by gas chromatography was found to be 99.7%.

| (1) Elemental Analysis (for C$_8$H$_{18}$N$_2$) | | | |
|---|---|---|---|
| | C | H | N |
| Calculated (%) | 67.55 | 12.76 | 19.69 |
| Found (%) | 67.30 | 13.00 | 19.49 |

(2) GC-MC Spectra

EI-MS Spectra: (M$^+$)=142. (Note: Molecular weight of ACEA (C$_8$H$_{18}$N$_2$)=142.2).

(3) IR Spectra (rock salt plate; neat):

IR Spectrum chart is shown in FIG. 1. cm$^{-1}$: 3300~3400; 2880~3050; 1610; 1460; 1380.

(4) $^1$H-NMR spectra (100 MHz, solvent: CDCl$_3$).

Figure 2:
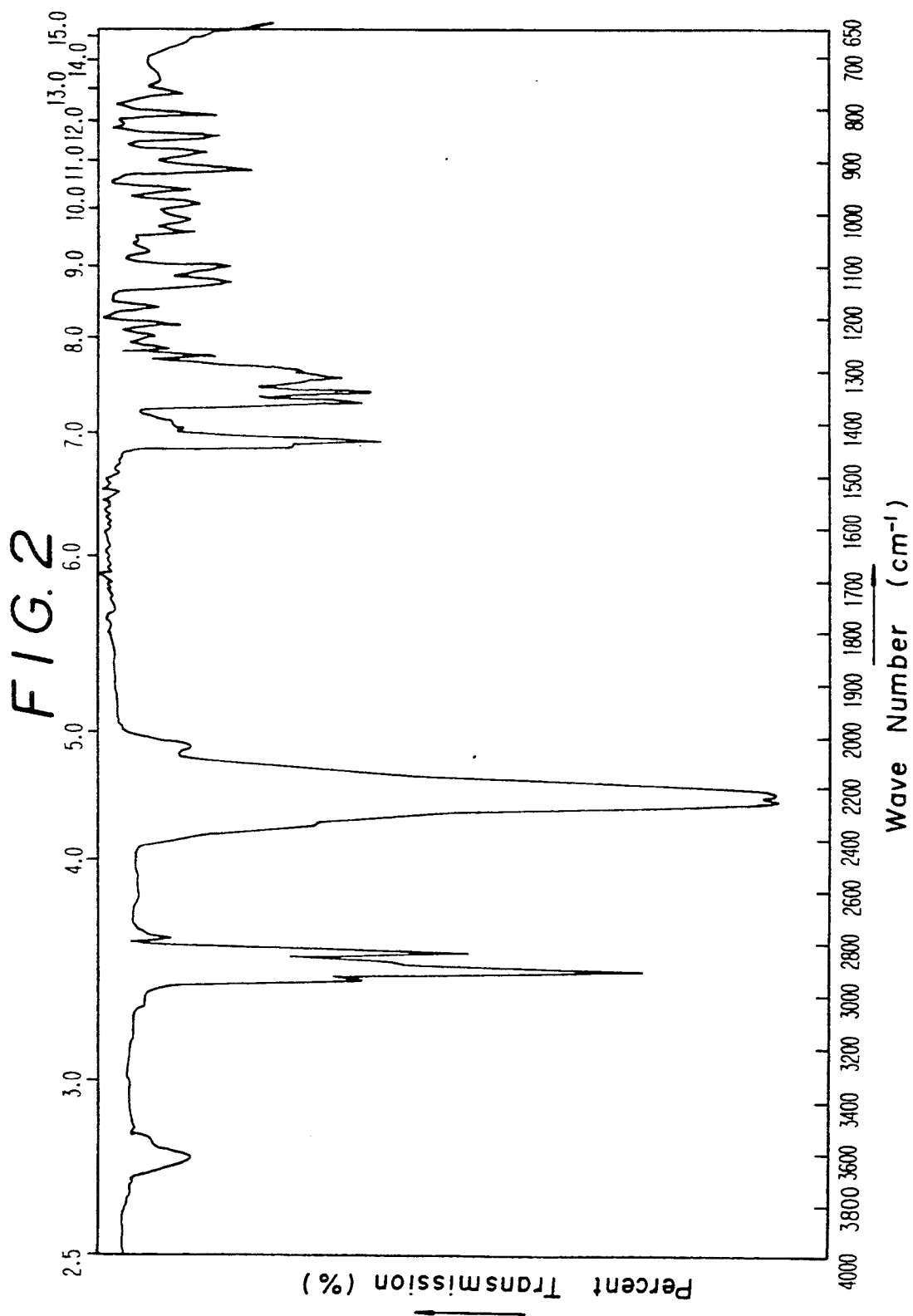
FIG. 2 is an IR chart observed on the α-(3-isocyanatocyclohexyl)ethylisocyanate obtained in Example 7.
Figure 3:
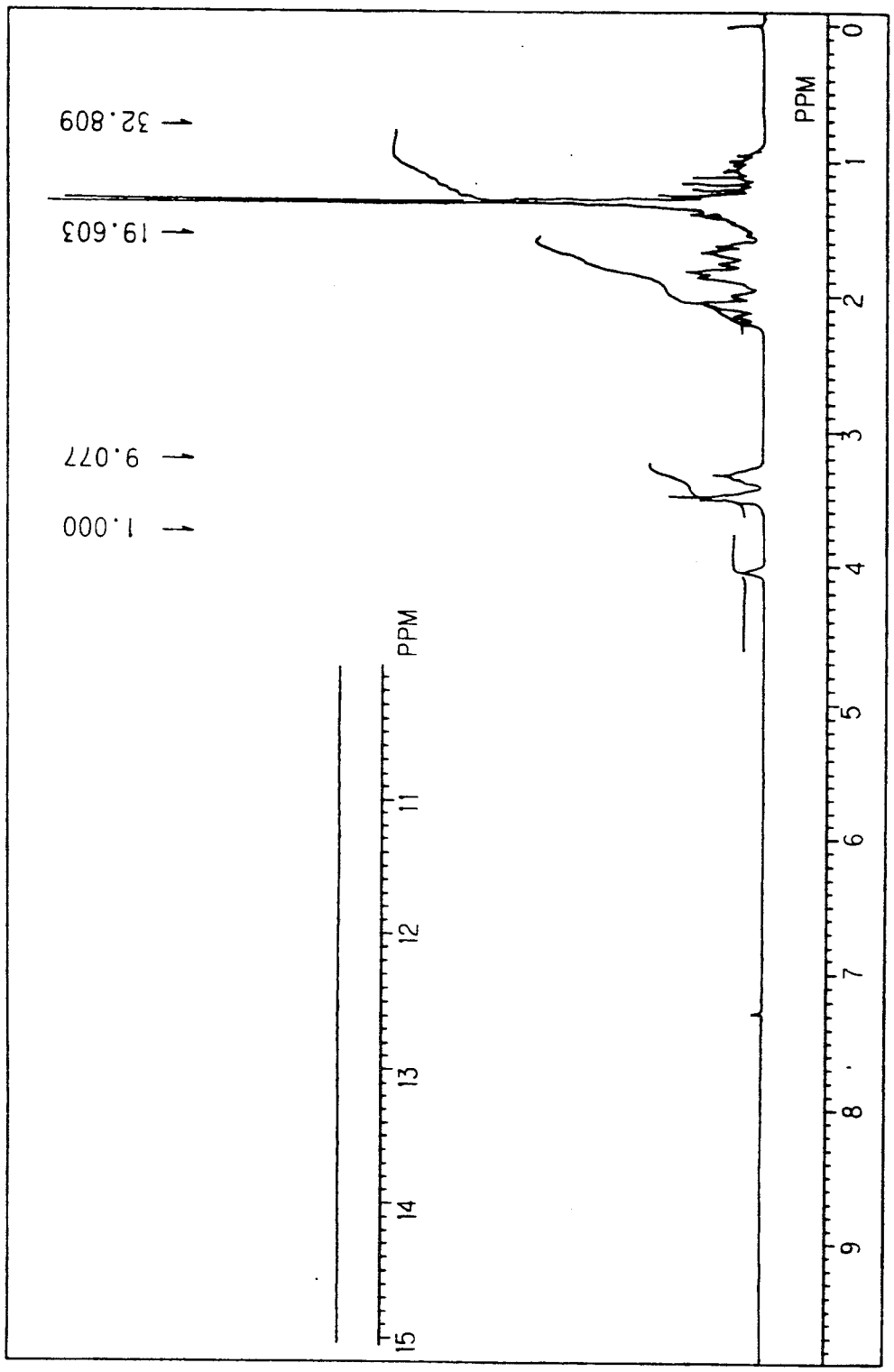
FIG. 3 is an NMR chart observed on the α-(3-isocyanatocyclohexyl)ethylisocyanate obtained in Example 7.

The NMR spectrum chart of the product is shown in FIG. 2.

COMPARATIVE EXAMPLE 1

The same procedures used in Example 1 were repeated except that water and the flake-like sodium hydroxide were not used, that the stirring was initiated when the temperature was raised to 110° C. and that the reaction mixture was stirred for about 12 hours at a hydrogen gas pressure of 80 to 70 kg/cm$^2$. The reaction solution was analyzed by gas chromatography and the yield of α-(3-aminocyclohexyl) ethylamine was found to be 20 mole % or less.

COMPARATIVE EXAMPLE 2

The same procedures used in Example 1 were repeated except that water was not used, that the stirring was initiated when the temperature was raised to 110° C. and that the reaction mixture was stirred for about 10 hours at a hydrogen gas pressure of 80 to 60 kg/cm$^2$. The reaction solution was analyzed by gas chromatography and the yield of α-(3-aminocyclohexyl)ethylamine was found to be 33 mole %.

EXAMPLE 2

Preparation of α-(3-aminocyclohexyl)ethylamine

To a 400 ml inner volume SUS 316L autoclave equipped with a stirring machine, there were added 50.2 g (0.369 mole) of α-(3-aminophenyl)ethylamine (APEA), 50 g 1,4-dioxane, 1.5 g (solid content) of 5% ruthenium/alumina catalyst and 2.5 g of sodium carbonate, the internal atmosphere was replaced with nitrogen gas. Then, hydrogen gas was introduced into the autoclave under pressure to a pressure of 40 kg/cm$^2$G and thereafter the temperature was raised up to 110° C. and then the stirring of the reaction mixture was initiated. Hydrogen gas was absorbed as the reaction proceeded during the temperature was raised to 200° C. and correspondingly hydrogen gas pressure was reduced. Thus, the reaction was continued while hydrogen gas was intermittently introduced so that the pressure thereof was maintained at a level ranging from 50 to 30 kg/cm$^2$G. During the reaction, the temperature was adjusted to 200° C. The absorption of hydrogen gas did not take place any more at the time when the total amount of hydrogen gas absorbed reached about 21.1N l and, therefore the reaction was stopped. The reaction mixture was cooled to room temperature, removed from the autoclave and filtered. After removing water from the filtrate by distillation in vacuo, distillation was further carried out at a pressure of 2 to 4 mmHg to obtain 32.2 g (yield 61.4%) of a distillate having a distillation range of 73° to 84° C.

As in Example 1, the resulting liquid was identified to be α-(3-aminocyclohexyl)ethylamine in terms of $^1$H-NMR spectra, GC-MC spectra and IR spectra. The result of elemental analysis are as follows:

| Elemental Analysis (for C$_8$H$_{18}$N$_2$) | | | |
|---|---|---|---|
| | C | H | N |
| Calculated (%) | 67.55 | 12.76 | 19.69 |
| Found (%) | 67.31 | 13.10 | 19.47 |

In addition, the purity of the product as determined by gas chromatography was found to be 99.7%.

The starting material, APEA, for preparing ACEA of the present invention was prepared according to the following reference Example 1.

REFERENCE EXAMPLE 1

Preparation of α-(3-aminophenyl)ethylamine

To a 500 ml inner volume SUS 316L autoclave equipped with a stirring machine, there were added 33.0 g (0.2 mole) of m-nitroacetophenone, 200 ml of methanol and 4.6 g (expressed in the amount of nickel) of Raney nickel, the internal atmosphere was replaced with nitrogen gas and the contents of the autoclave were stirred for a while.

While cooling the autoclave with ice-water, about 40 g of ammonia was added thereto. Then, hydrogen gas was introduced into the autoclave under pressure to a pressure of 40 kg/cm$^2$G and thereafter the temperature was raised up to 70° C. The reaction was continued at that temperature for 55 minutes. The absorption of hydrogen gas did not take place any more at the time when the total amount of hydrogen gas absorbed reached about 16.5 N l and, therefore, the reaction was stopped. The reaction mixture was cooled to room temperature, removed from the autoclave and filtered. Vacuum distillation was carried out at a pressure of 5 to 6 mmHg to obtain 23.9 g (yield 88.0%) of a distillate having a distillation range of 120° to 122° C.

The resulting liquid was colorless and clear and was identified to be α-(3-aminophenyl)ethylamine in terms of elemental analysis, GC-MC spectra, IR spectra, $^1$H-NMR spectra. The results thus observed are listed below. In addition, the purity thereof as determined by gas chromatography was found to be 99.3%.

| (1) $^1$H-NMR spectra (100 MHz, DMSO-d$_6$): δ ppm: | |
|---|---|
| 1.0~1.5: —CH$_3$ proton | 3H |
| 1.5~2.2: m-Ph-NH$_2$ | 2H |
| 3.6~4.1: —C—H | 1H |
| 4.2~5.3: —C—NH$_2$ | 2H |
| 6.1~7.2: protons of benzene ring | 4H |

(2) IR Spectra (rock salt plate; neat): cm$^{-1}$: 3400, 3340, 3190, 2940, 1600, 1485, 1455, 1360, 1310, 1160.

(2) GC-MC Spectra EI-MS Spectrum: (M$^+$)=136 (Note: Molecular weight of APEA (C$_8$H$_{12}$N$_2$)=136.2).

| (4) Elemental Analysis (for C$_8$H$_{12}$N$_2$) | | | |
|---|---|---|---|
| | C | H | N |
| Calculated (%) | 70.48 | 8.81 | 20.56 |
| Found (%) | 70.45 | 8.91 | 20.38 |

EXAMPLE 3

Preparation of α-(3-aminocyclohexyl)methylamine

The same procedures used in Example 1 were repeated except that 45.2 g (0.37 mole) of 3-aminobenzylamine was substituted for 3-APEA used in Example 1. After the reaction, the catalyst was removed and the water was removed from the reaction solution by distillation in vacuo. Then distillation was further performed at a pressure of 3 to 6 mmHg to obtain 41.5 g (yield 87%) of a distillate having a distillation range of from 80° to 90° C. This liquid was colorless and transparent and the purity of the product as measured by gas chromatography was found to be 99.3%. The result on elemental analysis is as follows:

| Elemental Analysis (for $C_7H_6N_2$) | | | |
|---|---|---|---|
| | C | H | N |
| Calculated (%) | 65.52 | 12.48 | 21.84 |
| Found (%) | 65.43 | 12.51 | 21.71 |

EXAMPLE 4

Preparation of α-(3-aminocyclohexyl)propylamine

The same procedures used in Example 1 were repeated except that 55.5 g (0.37 mole) of α-(3-aminophenyl)propylamine was substituted for 3-APEA used in Example 1. After the reaction, the catalyst was removed and the water was removed from the reaction solution by distillation in vacuo. Then distillation was further performed at a pressure of 3 to 6 mmHg to obtain 49.0 g (yield 85%) of a distillate having a distillation range of from 85° to 95° C. This liquid was colorless and transparent and the purity of the product as measured by gas chromatography was found to be 99.2%. The result on elemental analysis is as follows:

| Elemental Analysis (for $C_9H_{20}N_2$) | | | |
|---|---|---|---|
| | C | H | N |
| Calculated (%) | 69.14 | 12.80 | 17.93 |
| Found (%) | 69.00 | 12.85 | 17.81 |

EXAMPLE 5

Preparation of α-(aminocyclohexyl)ethylamine

The same procedures used in Example 1 were repeated except that 50.2 g (0.37 mole) of an APEA mixture which comprised 8.5 mole % of 2-isomer, 48.8 mole % of 3-isomer and 42.7 mole % of 4-isomer was substituted for 3-APEA used in Example 1. The resulting α-(aminocyclohexyl)ethylamine was analyzed by gas chromatography and found that it comprised 5.5 mole % of 2-isomer, 51.3 mole % of 3-isomer and 43.2 mole % of 4-isomer. After the reaction, the catalyst was removed and the water was removed from the reaction solution by distillation in vacuo. Then distillation was further performed at a pressure of 3 to 6 mmHg to obtain 43.1 g (yield 82.2%) of a distillate having a distillation range of from 83° to 93° C.

EXAMPLE 6

Preparation of α-(aminocyclohexyl)butylamine

The same procedures used in Example 5 were repeated except that 60.7 g (0.37 mole) of an α-(aminophenyl)butylamine mixture which comprised 7.1 mole % of 2-isomer, 53.9 mole % of 3-isomer and 39.0 mole % of 4-isomer was substituted for the APEA mixture used in Example 5 to obtain 50.7 g (yield 80.5%) of an α-(aminocyclohexyl)butylamine mixture.

EXAMPLE 7

Preparation of α-(isocyanatocyclohexyl)ethylisocyanate (hereunder referred to as "IECI")

To a 2 l reaction flask equipped with a stirring machine, a thermometer, a tube for introducing phosgene gas, a condenser and a dropping funnel, there was introduced 660 g of anhydrous toluene, the internal temperature of the flask was maintained at about 2° C. by immersing the flask in an ice-water bath with stirring and phosgene gas was introduced into the flask at a rate of 50 g/h over 90 minutes. Then a solution of 29.5 g (0.208 mole) of α-(3-aminocyclohexyl) ethylamine (ACEA) in 300 g of anhydrous toluene was dropwise added to the flask over 80 minutes. During the dropwise addition of the solution of ACEA in anhydrous toluene, cold phosgenation was performed at a temperature of 1° to 5° C. with the introduction of phosgene at a rate of 50 g/h and after completion of the dropwise addition, phosgene was further introduced at 5° to 7° C. at a rate of 50 g/h for additional 40 minutes.

After the dropwise addition of the ACEA-anhydrous toluene solution, a pale yellowish white slurry was formed in the flask. Then the temperature of the liquid in the flask was raised up to 86° C. over 2 hours while phosgene was introduced into the flask at a rate of 25 g/h. After raising the temperature, hot phosgenation was carried out at a temperature ranging from 86° to 108° C. for 6 hours while continuously introducing phosgene at a rate of 25 g/h. During the hot phosgenation, the liquid in the flask became a pale brown clear solution. The total amount of phosgene introduced during the cold-hot two-stage phosgenation was 375 g. This corresponds to 9.1 times the stoichiometric amount. Excess phosgene gas can be recovered by solvent-absorption. After the hot phosgenation, nitrogen gas was introduced into the reaction solution at a temperature of 103° to 104° C. at a flow rate of 650 ml/min for 2 hours 20 minutes to perform degassing.

After cooling the solution, the solvent, toluene, was removed by distillation under reduced pressure to thus obtain about 37 g of a brown reaction solution. The resultant solution was further purified by distillation under reduced pressure to thus recover about 30.3 g of a distillate having a boiling point of 139° C./7 mmHg (colorless transparent liquid; NCO content=43.2%). The result on elemental analysis of this distillate is as follows:

| Elemental Analysis (for $C_{10}H_{14}N_2O_2$) | | | |
|---|---|---|---|
| | C | H | N |
| Calculated (%) | 61.8 | 7.2 | 14.4 |
| Found (%) | 61.6 | 7.0 | 14.2 |

Moreover, in GC-MS spectrometry, it was found that $(M^+)$ was 194 which was well consistent with the molecular weight of the compound represented by $C_{10}H_{14}N_2O_2$. On the basis of the foregoing facts, the distillate was identified to be α-(3-isocyanatocyclohexyl)ethylisocyanate.

The resulting α-(3-isocyanatocyclohexyl)ethylisocyanate was a mixture of its trans- and cis-isomer and ratio of the amount of the trans-isomer to that of the cis-isomer was found to be 10:3 in terms of $^1$H-NMR spectroscopy measurement.

EXAMPLE 8

Preparation of IECI

To the same 2 l reaction flask used in Example 7, there was introduced 870 g of butyl acetate, the internal temperature of the flask was maintained at about 2° C. by immersing the flask in an ice-water bath with stirring and phosgene gas was introduced into the flask at a rate of 65 g/h over one hours. Then a solution of 41.5 g (0.292 mole) of ACEA in 374 g of butyl acetate was dropwise added to the flask over 105 minutes. During the dropwise addition of the solution of ACEA in butyl acetate, cold phosgenation was performed at a temperature of 3° to 8° C. with the introduction of phosgene at a rate of 57 g/h and after completion of the dropwise addition, phosgene was further introduced at 8° to 11° C. at a rate of 50 g/h over 15 minutes.

After the dropwise addition of the ACEA-butyl acetate solution, a pale yellowish white slurry was formed in the flask. Then the temperature of the liquid in the flask was raised up to 86° C. over 130 minutes while phosgene was introduced into the flask at a rate of 25 g/h. After raising the temperature, hot phosgenation was carried out at a temperature ranging from 86° to 120° C. for 8 hours 40 minutes while continuously introducing phosgene at a rate of 25 g/h. During the hot phosgenation, the liquid in the flask became an almost clear solution, but a small amount of insoluble matter remained. Thus, nitrogen gas was blown through the solution at 120° C. for 2 hours, after the hot phosgenation, to perform degassing, the solution was cooled and then filtered to remove the insoluble matter. The solvent, butyl acetate, was removed from the solution, from which the insoluble matter was removed, by distillation under reduced pressure to thus obtain about 50 g of a brown reaction solution. The resultant solution was further purified by distillation under reduced pressure to thus recover about 43.0 g of a distillate having a boiling point of 142° C./8 mmHg (colorless transparent liquid; NCO content=43.2%). The result on elemental analysis of this distillate is as follows:

| | Elemental Analysis | | |
|---|---|---|---|
| | C | H | N |
| Calculated (%) | 61.7 | 7.0 | 14.3 |
| Found (%) | 61.8 | 7.2 | 14.4 |

IR spectra and $^1$H-NMR spectra: The same results observed in Example 7 were obtained.

EXAMPLE 9

Preparation of IECI

In this Example, phosgenation was performed according to a hydrochloride process. o-Dichlorobenzene was used as a solvent. A solution of 42.7 g (0.30 mole) of ACEA in 1,150 g of o-dichlorobenzene was introduced into the same 2 l reaction flask used in Example 7 and cooled to 18° C. with stirring. Then hydrogen chloride gas was bubbled into the solution to form hydrochlorides. As the hydrochloride was formed, the temperature of the solution was raised and correspondingly the solution was cooled so that the temperature was maintained at not higher than 35° C. After 90 minutes, the introduction of hydrogen chloride gas was stopped, and the temperature of the resulting hydrochloride slurry was raised to 125° C. over 90 minutes while blowing phosgene gas into the slurry at a rate of 50 g/h. Further, phosgene gas was introduced at a rate of 50 g/h at that temperature for 9 hours. At this stage, the reaction solution became almost clear and thus the introduction of phosgene was stopped and nitrogen gas was bubbled into the solution at 125° C. for 2 hours to perform degassing. After cooling the reaction solution which had been degassed was filtered to remove a small amount of insoluble matter and then the solvent, o-dichlorobenzene, was removed by distillation under reduced pressure to thus recover about 54 g of a brown liquid. The liquid was further purified by distillation under reduced pressure to obtain about 45.6 g of a distillate having a boiling point of 142° C./8 mmHg (colorless transparent liquid; NCO content=43.1%). The results on the measurements of IR spectra and $^1$H-NMR spectra as well as elemental analysis were almost consistent with those for the product in Example 7.

EXAMPLE 10

Preparation of α-(3-isocyanatocyclohexyl)methylisocyanate

In this Example, phosgenation was likewise performed according to a hydrochloride process. Amyl acetate was used as a solvent. 460 g of amyl acetate was introduced into a 1 l reaction flask and hydrogen chloride gas was introduced into the amyl acetate at a rate of 36 g/h for about 45 minutes while cooling the flask to a temperature of about 0° to 5° C. by immersing it in an ice-water bath with stirring. Then a solution of 32.1 g (0.25 mole) of α-(3-aminocyclohexyl) methylamine in 303 g of amyl acetate was dropwise added to the solution over 90 minutes. During the dropwise addition, the temperature of the contents was maintained at 5° to 12° C. while introducing hydrogen chloride gas at a rate of 30 g/h to thus form hydrochlorides. After the dropwise addition of the amine solution, hydrogen chloride gas was bubbled into the solution at a rate of 30 g/h for additional 30 minutes. At this stage, the introduction of hydrogen chloride gas was stopped, and the temperature of the resulting hydrochloride slurry was raised to 110° C. over about 60 minutes while blowing phosgene gas into the slurry at a rate of 50 g/h. Further, phosgenation reaction was continued by introducing phosgene at a rate of 50 g/h at a temperature of 110° to 125° C. for 2 hours and at a temperature of 125° to 137° C. for 3.5 hours. At this stage, the reaction solution became almost clear and thus the introduction of phosgene was stopped and nitrogen gas was bubbled into the solution at 136° C. for 2 hours to perform degassing. After cooling the reaction solution which had been degassed, it was filtered to remove a small amount of insoluble matter and then the solvent, amyl acetate, was removed by distillation under reduced pressure to thus recover about 45 g of a brown liquid. The liquid was further purified by distillation under reduced pressure (1 to 2 mmHg) to obtain about 38 g of a distillate having a distillation range of 112° to 115° C. (colorless transparent liquid; NCO content=46.55%). The purity of this distillate as determined by gas chromatography was found to be 99.51%. The result on elemental analysis is given below.

| Elemental Analysis (for C₉H₁₂N₂O₂) | | | |
|---|---|---|---|
| | C | H | N |
| Calculated (%) | 59.93 | 6.66 | 15.54 |
| Found (%) | 59.81 | 6.70 | 15.40 |

EXAMPLE 11

Preparation of
α-(3-isocyanatocyclohexyl)propylisocyanate

The same procedures used in Example 10 were repeated except that 39.1 g (0.25 mole) of α-(3-aminocyclohexyl)propylamine was substituted for 32.1 g of α-(3-aminocyclohexyl)methylamine used in Example 10 to obtain about 49 g of a brown reaction liquid. The liquid was further purified by distillation under reduced pressure (1 to 2 mmHg) to thus recover 44.7 g of a distillate having a distillation range of from 116° to 120° C. (colorless transparent liquid; content of NCO=40.3%).

The purity of this distillate as determined by gas chromatography was found to be 99.7%. The result on elemental analysis is given below.

| Elemental Analysis (for C₁₁H₁₆N₂O₂) | | | |
|---|---|---|---|
| | C | H | N |
| Calculated (%) | 63.40 | 7.68 | 13.45 |
| Found (%) | 63.20 | 7.70 | 13.40 |

EXAMPLE 12

Preparation of
3-(α-isocyanatocyclohexyl)ethylisocyanato-isocyanurate (hereunder referred to as "IECI-isocyanurate")

(1) Preparation of a mixture of catalyst or the like (catalyst B)

The following catalyst and the like were prepared.

| Trimerization catalyst | |
|---|---|
| Potassium acetate | 2.0 g (2.56 × 10⁻² mole) |
| Potassium cyanate | 0.4 g (0.65 × 10⁻² mole) |
| Co-catalyst | |
| Polyethylene glycol #400 (MW = 400) | 18.0 g (4.5 × 10⁻² mole) |
| Stabilizer | |
| 2,6-Di-t-butyl-4-methylphenol | 0.2 g (9.62 × 10⁻⁴ mole) |
| Triphenyl phosphite | 0.2 g (6.45 × 10⁻⁴ mole) |
| Solvent | |
| Butyl acetate | 20.0 g |
| Total | 40.8 g |

(2) Preparation of Stopping agent C

This was prepared by dissolving 0.5 g (as H₃PO₄; 5.1 × 10⁻³ mole) in 25 g of butyl acetate.

(3) Preparation of IECI-isocyanurate

To a 30 ml four-necked flask, there were added 10.0 g of IECI (obtained by phosgenation of α-(3-aminocyclohexyl)ethylamine) and 3.3 g of butyl acetate as a solvent to dissove the former in the latter and the temperature was adjusted to 25° C. with stirring in a nitrogen gas blanket. 0.4 g of the catalyst B prepared above was added thereto, then the flask was externally warmed to control the temperature of the solution to 70° C.

When the amount of unreacted free IECI was determined by gas chromatography on each sample of the reaction solution collected periodically, 8 hours after the addition of the catalyst B, the amount of free IECI was reduced to about 37%. At this stage, 0.75 g of the stopping agent C was added to the reaction system, stirring was continued for additional one hour and then the stirring was stopped to remove the contents of the flask.

The weight of the contents removed was 14.0 g.

After removing excess IECI and the solvent by distillation under reduced pressure, 5.1 g of the resulting pale yellowish white solids were again dissolved in 5.1 g of butyl acetate.

The composition of this solution was as follows:

| | |
|---|---|
| Solid contents (non-volatile matter) | 50.0% by weight |
| NCO content | 9.1% by weight |
| Free IECI | 0.8% by weight |
| Chlorine capable of causing hydrolysis | 0.011% by weight |

The product was reacted with methyl alcohol to form a methylcarbamate compound thereof and the methylcarbamate compound was analyzed by GPC. As a result, it is found that the product comprised the following oligomers in amounts described below:

| | |
|---|---|
| n = 1 (trimer) | 43.8% |
| n = 2 (pentamer) | 20.6% |
| n = 3 (heptamer) | 13.2% |
| n = 4 and 5 | 22.4% |

Figure 4:
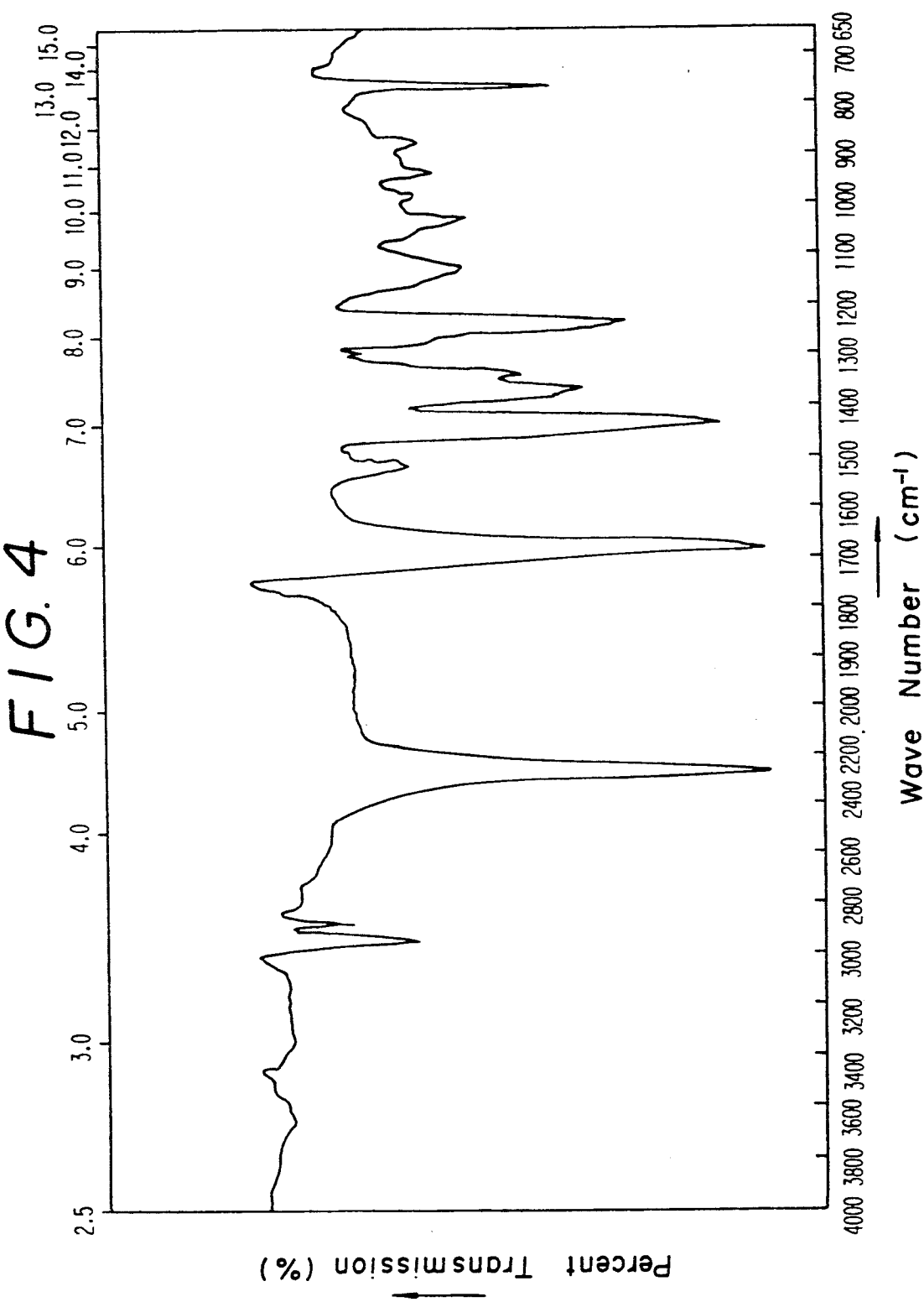
FIG. 4 is an IR chart observed on the polyisocyanato-isocyanurate prepared in Example 12.

FIG. 4 shows the result of IR spectrometric measurement of this product (rock salt plate; (50% by weight) solution; control solution: a butyl acetate solution).

Absorptions observed at 1400 to 1420 cm⁻¹ and 1690 to 1700 cm⁻¹ are the absorption bands due to the isocyanurate ring and that observed at 2220 to 2230 cm⁻¹ is the absorption band due to the presence of the isocyanato group.

EXAMPLE 13

To a flask similar to that used in Example 12, there were added 20.0 g of IECI and 6.6 g of butyl acetate and the mixture was stirred in a nitrogen gas blanket to control the temperature to 25° C.

To the solution, there was added 0.6 g of a catalyst B (prepared in the same manner as in Example 12), then the flask was externally warmed to control the temperature of the solution to 60° C. When the amount of unreacted free IECI was determined by gas chromatography on each sample of the reaction solution collected periodically, 12 hours after the addition of the catalyst B, the amount of free IECI was reduced to about 34%. At this stage, 1.1 g of a stopping agent C (prepared in the same manner as in Example 12) was added to the reaction system, stirring was continued for additional one hour at a temperature of 50° C. and then the stirring was stopped to remove the contents of the flask.

The weight of the contents removed was 26.0 g.

After removing excess IECI and the solvent by distillation under reduced pressure, 10.7 g of the resulting pale yellowish white solids were again dissolved in 10.7 g of butyl acetate.

The composition of this solution was as follows:

| | |
|---|---|
| Solid contents (non-volatile matter) | 50.0% by weight |
| NCO content | 9.2% by weight |

| -continued | |
|---|---|
| Free IECI | 1.0% by weight |

The product was reacted with methyl alcohol to form a methylcarbamate compound thereof and the methylcarbamate compound was analyzed by GPC. As a result, it is found that the product comprised the following oligomers in amounts described below:

| n = 1 (trimer) | 39.0% |
|---|---|
| n = 2 (pentamer) | 23.1% |
| n = 3 to 5 | 37.9% |

EXAMPLE 14

Preparation of [(3-isocyanatocyclohexyl) methylisocyanate]-isocyanurate (hereunder referred to as "ICMI-isocyanurate")

To a flask similar to that used in Example 12, there were added 10.0 g (0.056 mole) of (3-isocyanatocyclohexyl)methylisocyanate (prepared by phosgenating (3-aminocyclohexyl)methylamine: hereinafter referred to as "ICMI") and 3.3 g of butyl acetate and the temperature was adjusted to 25° C. with stirring in a nitrogen gas blanket. 0.4 g (0.00031 mole) of a catalyst B (prepared in the same manner as in Example 12) was added thereto, then the flask was externally warmed or cooled to control the temperature of the solution to 70° C.

When the amount of unreacted free ICMI was determined by gas chromatography on each sample of the reaction solution collected periodically, 6 hours after the addition of the catalyst B, the amount of free ICMI was reduced to not higher than 35%. At this stage, 0.75 g (0.00015 mole) of a stopping agent C (prepared in the same manner as in Example 12) was added to the reaction system, stirring was continued for additional one hour at a temperature of 60° C. and then the stirring was stopped to remove the contents of the flask.

The weight of the contents removed was 10.1 g.

After removing excess ICMI and the solvent by distillation under reduced pressure, 4.8 g of the resulting pale yellowish white solids were again dissolved in 4.8 g of butyl acetate.

The composition of this solution was as follows:

| Solid contents (non-volatile matter) | 50.0% by weight |
|---|---|
| NCO content | 10.1% by weight |
| Free IECI | 1.1% by weight |
| Chlorine capable of causing hydrolysis | 0.01% by weight |

The product was reacted with methyl alcohol to form a methylcarbamate compound thereof and the methylcarbamate compound was analyzed by GPC. As a result, it is found that the product comprised the following oligomers in amounts described below:

| n = 1 (trimer) | 55.4% |
|---|---|
| n = 2 (pentamer) | 21.4% |
| n = 3 (heptamer) | 9.7% |
| n = 4 and 5 | 12.3% |

EXAMPLE 15

Preparation of [(3(4)-isocyanatocyclohexyl) methylisocyanate]-isocyanurate

To a flask similar to that used in Example 12, there was added 10.0 g (0.056 mole) of a mixture of (3-isocyanatocyclohexyl) methylisocyanate and (4-isocyanatocyclohexyl)methylisocyanate (obtained by phosgenation of a mixture of (3-aminocyclohexyl) methylamine and (4-aminocyclohexyl)methylamine; hereunder referred to as "ICMI") and 3.3 g of butyl acetate to dissolve the former in the latter and the temperature was adjusted to 25° C. with stirring in a nitrogen gas blanket. 0.4 g (3.2×10$^{-4}$ mole) of a catalyst B (prepared in the same manner as in Example 12) was added thereto, then the flask was externally warmed or cooled to control the temperature of the solution to 60° C.

When the amount of unreacted free ICMI was determined by gas chromatography on each sample of the reaction solution collected periodically, 12 hours after the addition of the catalyst B, the amount of free ICMI was reduced to not higher than 35%. At this stage, 0.75 g (8.83×10$^{-5}$ mole) of a stopping agent C (prepared in the same manner as in Example 12) was added to the reaction system, stirring was continued for additional one hour at 60° C. and then the stirring was stopped to remove the contents of the flask. The weight of the contents removed was 10.1 g. After removing excess ICMI and the solvent by distillation under reduced pressure, 4.9 g of the resulting pale yellowish white solids were again dissolved in 4.9 g of butyl acetate. The composition of this solution was as follows:

| Solid contents (non-volatile matter) | 50.0% by weight |
|---|---|
| NCO content | 10.3% by weight |
| Free IECI | 1.1% by weight |
| Chlorine capable of causing hydrolysis | 0.009% by weight |

The product was reacted with methyl alcohol to form a methylcarbamate compound thereof and the methylcarbamate compound was analyzed by GPC. As a result, it is found that the product comprised the following oligomers in amounts described below:

| n = 1 (trimer) | 60.3% |
|---|---|
| n = 2 (pentamer) | 22.0% |
| n = 3 (heptamer) | 10.5% |
| n = 4 and 5 | 7.2% |

REFERENCE EXAMPLE 2

Preparation of Acryl Polyol Resin

A mixed monomer liquid which comprised 150 g of 2-hydroxyethyl methacrylate, 50 g of methyl methacrylate, 150 g of n-butyl methacrylate, 25 g of n-butyl acrylate, 125 g of styrene, 15 g of acrylic acid, 25 g of diethylene glycol and 50 g of t-butylperoxy-2-ethylhexanoate was dropwise added continuously, over 2 hours, to 1,200 g of n-butyl acetate which had been refluxed, and the reflux was continued for additional 5 hours to polymerize the monomers. After completion of the polymerization reaction, a part of the n-butyl acetate was distilled off to adjust the concentration of the solid content to 80%. The acryl polyol solution thus prepared had a viscosity of 6,500 cp/25° C., a number average molecular weight of 1,300 and a hydroxyl value of 92 KOH mg/g.

REFERENCE EXAMPLE 3L

Preparation of Base Enamel

Base enemal was prepared by compounding the acryl polyol solution prepared in Reference Example 2 as described below.

| | |
|---|---|
| The acryl polyol prepared in Reference Example 2 | 45 g |
| Pigment: Titanium oxide R930 (available from Ishihara Sangyo Co.) | 45 g |
| Thinner (a mixed solution of xylene/toluene/butyl acetate/methyl ethyl ketone) | 10 g |

The above components were blended in the proportion listed above and the pigment was kneaded into the blend with a three-roll mill to obtain an intended base enamel.

EXAMPLES 16 TO 18 AND COMPARATIVE EXAMPLES 3 to 6

Compositions for forming urethane resins according to the present invention was prepared by compounding each of solutions of isocyanurate type polisocyanates obtained in Examples 12, 14 and 15, the acryl polyol resin solution as shown in Reference Example 2 and the base enamel prepared in Reference Example 3 so that the molar amount of the isocyanato group was equal to that of the hydroxyl group and the content of pigments (PWC) was 40% by weight; adding a thinner comprising ethyl acetate/toluene/butyl acetate/xylene/cellosolve acetate (weight ratio=30/30/20/15/5) and then adjusting to 15 sec./25° C. with Ford-Cup #4.

The resulting composition was coated on the surface of steel plates and glass plates with an air spray gun (IWATANI-77 Model; nozzle diameter 2 mm ⌀) so that the thickness of the film determined after drying was 25μ, allowed to stand at room temperature (20° C./60% RH) for 7 days and was used in the following tests.

For comparison, the same tests were also carried out using conventional samples, i.e., an organic polyisocyanate derived from tolylene diisocyanate (OLESTER P75 available from MITSUI TOATSU CHEMICALS, INC.) and three kinds of aliphatic polyisocyanates: (1) OLESTER NP1000 (available from MITSUI TOATSU CHEMICALS, INC.); (2) CORONATE EH (an isocyanurate derivative of hexamethylene diisocyanate available from NIPPON POLYURETHANE CO., LTD.); and (3) IPDI T1890 (DAICEL . HUELS Co., Ltd.). Coated film performance and physical properties of these samples are listed in the following Table 1.

The tests on the properties of the coated films were performed at 20° C./60% RH and they were evaluated according to JIS K-5400. In Table 1, 1) to 9) are as follows:

1) Adhesion: determined according to JIS D-0202.

2) Erichsen extrusion: determined according to JIS Z-2247.

3) Magic staining properties: determined according to JAS 1373. More specifically, a test piece is horizontally placed, a line of 10 mm wide was drawn on the surface of the test piece with a quick-drying ink defined in JIS S-6037(1964), allowed to stand for 24 hours and then wiped off with a cloth containing an alcohol. The results are estimated according to the following three stage evaluation standard.

○: there remains no mark; Δ: there remains slight mark; X: there remains clear mark.

4) Xylene rubbing (50 times): A test piece was fixed on a tester for fastness to rubbing of dyed materials and cotton cloth containing 2 ml of xylene was moved back and forth for 50 times under a load of 500 g. The result is estimated according to the following three stage evaluation:

○: no abnormality; Δ: there remains slight rubbing mark; X: the surface of the substrate can be seen.

5) Resistance to acids and alkalis: determined according to JAS 1373. More specifically, a test piece is horizontally placed, a 10% aqueous sulfuric acid solution (or a 10% aqueous sodium hydroxide solution) is dropwise added to the surface of the test piece, the surface is covered with a watch glass for 24 hours and then allowed to stand for 24 hours. The result is estimated according to the following three stage evaluation:

○: no abnormality; Δ: there remains slight mark; X: there remains clear mark.

6) WOM degree of yellowing: determined according to JIS K-7103.

7) Gloss (60° gloss): determined according to JIS K-5400.

8) Du-Pont impact (½ in/500 g): determined according to JIS K-5400.

9) Secondary Physical properties: After a sample is immersed in boiling water for 4 hours, physical properties are determined.

EXAMPLE 19 AND COMPARATIVE EXAMPLES 7 TO 10

The same tests as those in Example 16 were performed on a typical commercially available acryl polyol resin, i.e., OLESTER Q 182 (MITSUI TOATSU CHEMICALS, INC.; number average molecular weight=9,500; content of solids=50%; hydroxyl value=45 KOHmg/g). The same procedures used in Example 16 were repeated except that a different compound having active hydrogen atoms was employed.

On the other hand, the same tests were performed on the four kinds of the aliphatic polyisocyanates used in Comparative Examples 3 to 6. The results obtained are summarized in the following Table 2.

Tests on quality of coated films and methods for evaluation were the same as those employed in Example 16.

EXAMPLE 20 AND COMPARATIVE EXAMPLES 11 TO 14

The same tests as those in Example 16 were performed on a commercially available polyester polyol resin, i.e., OLESTER Q 173 (MITSUI TOATSU CHEMICALS, INC.; content of solids=100%; hydroxyl value=256 KOHmg/g). The same procedures used in Example 16 were repeated except that a different compound having active hydrogen atoms was employed.

On the other hand, the same tests were performed on the four kinds of the aliphatic polyisocyanates used in Comparative Examples 3 to 6. The results obtained are summarized in the following Table 3.

Tests on quality of coated films and methods for evaluation were the same as those employed in Example 16.

EXAMPLE 21

The same tests used in Example 19 were performed on a sample which had the same composition as that used in Example 16 except that an organic polyisocyanate component used was a solution of the isocyanurate type polyisocyanate solution obtained in Example 12 to which commercially available OLESTER NP 1000 (1/1 weight ratio) was added. The results obtained are listed in the following Table 2.

Tests on quality of coated films and methods for evaluation were the same as those employed in Example 16.

EXAMPLE 22

The same tests used in Example 19 were performed on a sample which had the same composition as that used in Example 16 except that an organic polyisocyanate component used was a solution of the isocyanurate type polyisocyanate solution obtained in Example 12 to which commercially available OLESTER NP 1000 (1/5 weight ratio) was added. The results obtained are listed in the following Table 2.

Tests on quality of coated films and methods for evaluation were the same as those employed in Example 16.

TABLE 1

|  | Example 16 | Example 17 | Example 18 | Comp. Ex. 3 | Comp. Ex. 4 | Comp. Ex. 5 | Comp. Ex. 6 |
|---|---|---|---|---|---|---|---|
| Compounding | | | | | | | |
| Isocyanate | Example 12 | Example 14 | Example 15 | OLESTER NP1000 | CORONATE EH | IPDI T = 1890 | OLESTER P75 |
| Active H-containing compound | Acryl polyol of Reference Example 2 and base enamel of reference Example 3 | | | | | | |
| Compatibility | good | good | good | good | good | good | good |
| Reactivity | | | | | | | |
| Set to touch (min.) | 10 | 9 | 9 | 13 | 13 | 15 | 8 |
| Complete hardening (min.) | 225 | 220 | 220 | 300 | 300 | 270 | 100 |
| Pot life (hr.) | ≧24 | ≧24 | ≧24 | ≧24 | ≧24 | ≧24 | 20 |
| Film appearance | good | good | good | good | good | good | good |
| Film thickness (μ) | 22.7 | 23.4 | 24.7 | 24.3 | 23.8 | 24.1 | 25.4 |
| Gloss (60° gloss) 7) | 92 | 92 | 93 | 92 | 89 | 88 | 85 |
| Erichsen extrusion (cm) 2) | ≧8 | ≧8 | ≧8 | ≧8 | ≧8 | 7.29 | 3.27 |
| DuPont impact (½ in/500 g) 8) | ≧50 | ≧50 | ≧50 | ≧50 | ≧50 | ≧50 | 25 |
| Magic ink staining 3) | | | | | | | |
| (Red) | ○ | ○ | ○ | Δ | ○ | ○ | ○ |
| (Black) | ○ | ○ | ○ | Δ | Δ | Δ | ○ |
| (Blue) | ○ | ○ | ○ | Δ | ○ | X | ○ |
| Xylene rubbing (50 times) 4) | ○ | ○ | ○ | Δ | Δ | Δ | ○ |
| Adhesion 1) | 100/100 | 100/100 | 100/100 | 100/100 | 100/100 | 100/100 | 50/100 |
| Pencil hardness | H | H | H | F | H | H | H |
| Resistance to acid 5) | ○ | ○ | ○ | ○ | ○ | ○ | ○ |
| Resistance to alkali 5) | ○ | ○ | ○ | ○ | ○ | ○ | ○ |
| Secondary physical properties | | | | | | | |
| Appearance | no change | no change | no change | no change | no change | no change | no change |
| Gloss (60° gloss) 7) | 90 | 90 | 90 | 89 | 88 | 85 | 82 |
| Erichsen extrusion (cm) 2) | 1.02 | 1.21 | 1.53 | 5.35 | 4.76 | 0.53 | 0.28 |
| DuPont impact (½ in/500 g) 8) | 30 | 30 | 30 | 45 | 40 | 20 | 10 |
| Adhesion 1) | 100/100 | 100/100 | 100/100 | 100/100 | 100/100 | 100/100 | 0/100 |
| WOM degree of yellowing(ΔE) 6) | | | | | | | |
| 200 hrs. | 0.48 | 0.52 | 0.51 | 0.45 | 0.42 | 0.52 | 3.62 |
| 500 hrs. | 0.84 | 0.92 | 0.91 | 0.85 | 0.73 | 0.91 | 4.53 |
| 1000 hrs. | 1.53 | 1.73 | 1.81 | 2.13 | 1.69 | 2.02 | 5.68 |

TABLE 2

|  | Example 19 | Comp. Ex. 7 | Comp. Ex. 8 | Comp. Ex. 9 | Comp. Ex. 10 | Example 21 | Example 22 |
|---|---|---|---|---|---|---|---|
| Compounding | | | | | | | |
| Isocyanate | Example 12 | OLESTER NP1000 | CORONATE EH | IPDI T = 1890 | OLESTER P75 | Ex. 12/ OLESTER NP1000 = 1/1 | Ex. 12/ OLESTER NP1000 = 1/5 |
| Content of IECI isocyanurate type polyisocyanate in the total amount of organic polyisocyanate (wt %) | 100 | 0 | 0 | 0 | 0 | 40 | 12 |
| Active H-containing compound | | | | OLESTER Q182 | | | |
| Compatibility | good | good | good | good | good | good | good |
| Reactivity | | | | | | | |
| Set to touch (min.) | 8 | 21 | 19 | 17 | 7 | 15 | 19 |
| Complete hardening (min.) | 47 | 60 | 58 | 56 | 30 | 50 | 57 |
| Pot life (hr.) | ≧24 | ≧24 | ≧24 | ≧24 | 10 | ≧24 | ≧24 |
| Film appearance | good | good | good | good | good | good | good |
| Film thickness (μ) | 22.0 | 21.7 | 23.0 | 22.5 | 23.5 | 23.0 | 22.7 |
| Gloss (60° gloss) 7) | 93.7 | 88.2 | 84.4 | 85.0 | 83.2 | 90.7 | 85.3 |
| Erichsen extrusion (cm) 2) | 2.51 | 7.45 | 7.67 | 0.10 | 0.12 | 4.27 | 6.23 |
| DuPont impact (½ in/500 g) 8) | 20 | 30 | 15 | 15 | 10 | 20 | 30 |
| Magic ink staining 3) | | | | | | | |
| (Red) | ○ | Δ | ○ | X | ○ | ○ | Δ |
| (Black) | ○ | X | Δ | X | ○ | Δ | X |
| (Blue) | ○ | X | Δ | X | ○ | ○ | Δ |

TABLE 2-continued

|  | Example 19 | Comp. Ex. 7 | Comp. Ex. 8 | Comp. Ex. 9 | Comp. Ex. 10 | Example 21 | Example 22 |
|---|---|---|---|---|---|---|---|
| Xylene rubbing (50 times) 4) | ○ | Δ | Δ | X | ○ | ○ | Δ |
| Adhesion 1) | 100/100 | 100/100 | 100/100 | 100/100 | 100/100 | 100/100 | 100/100 |
| Pencil hardness | 2H | H | 2H | H | 2H | 2H | H |
| Resistance to acid 5) | ○ | ○ | ○ | ○ | ○ | ○ | ○ |
| Resistance to alkali 5) | ○ | ○ | ○ | ○ | ○ | ○ | ○ |
| Secondary physical properties |  |  |  |  |  |  |  |
| Appearance | no change | no change | no change | no change | no change | no change | no change |
| Gloss (60° gloss) 7) | 88.5 | 84.0 | 84.4 | 84.5 | 82.2 | 84.2 | 84.3 |
| Erichsen extrusion (cm) 2) | 0.51 | 5.34 | 6.42 | 0.12 | 0.20 | 2.35 | 4.20 |
| DuPont impact (½ in/500 g) 8) | 20 | 25 | 25 | 20 | 10 | 20 | 25 |
| Adhesion 1) | 100/100 | 100/100 | 100/100 | 70/100 | 0/100 | 100/100 | 100/100 |
| WOM degree of yellowing(ΔE) 6) |  |  |  |  |  |  |  |
| 200 hrs. | 0.44 | 0.35 | 0.42 | 0.53 | 3.82 | 0.65 | 0.47 |
| 500 hrs. | 0.77 | 0.78 | 0.65 | 0.82 | 4.57 | 0.63 | 0.85 |
| 1000 hrs. | 1.56 | 2.15 | 1.88 | 2.25 | 5.29 | 1.72 | 1.94 |

TABLE 3

|  | Example 20 | Comp. Ex. 11 | Comp. Ex. 12 | Comp. Ex. 13 | Comp. Ex. 14 |
|---|---|---|---|---|---|
| Compounding |  |  |  |  |  |
| Isocyanate | Example 12 | OLESTER NP1000 | CORONATE EH | IPDI T = 1890 | OLESTER P75 |
| Active H-containing compound |  |  | OLESSTER Q173 |  |  |
| Compatibility | good | good | good | good | good |
| Reactivity |  |  |  |  |  |
| Set to touch (min.) | 60 | 69 | 69 | 78 | 55 |
| Complete hardening (hr.) | 20 | 24 | 24 | 25 | 9.5 |
| Pot life (hr.) | ≧48 | ≧48 | ≧48 | ≧48 | 22 |
| Film appearance | good | good | good | good | good |
| Film thickness (μ) | 25.9 | 26.7 | 25.2 | 24.9 | 25.7 |
| Gloss (60° gloss) 7) | 98.3 | 98.9 | 98.0 | 98.5 | 98.3 |
| Erichsen extrusion (cm) 2) | ≧8 | ≧8 | ≧8 | ≧8 | ≧8 |
| DuPont impact (½ in/500 g) 8) | ≧50 | ≧50 | ≧50 | ≧50 | ≧50 |
| Magic ink staining 3) |  |  |  |  |  |
| (Red) | Δ | X | X | X | ○ |
| (Black) | Δ | X | X | X | ○ |
| (Blue) | ○ | X | Δ | X | ○ |
| Xylene rubbing (50 times) 4) | Δ | X | Δ | X | ○ |
| Adhesion 1) | 100/100 | 100/100 | 100/100 | 100/100 | 0/100 |
| Pencil hardness | F | B | F | B | H |
| Resistance to acid 5) | ○ | ○ | ○ | ○ | ○ |
| Resistance to alkali 5) | ○ | ○ | ○ | ○ | ○ |
| Secondary physical properties |  |  |  |  |  |
| Appearance | no change | no change | no change | no change | no change |
| Gloss (60° gloss) 7) | 97.5 | 97.3 | 96.2 | 96.2 | 97.1 |
| Erichsen extrusion (cm) 2) | ≧8 | ≧8 | ≧8 | ≧8 | 3.91 |
| DuPont impact (½ in/500 g) 8) | ≧50 | ≧50 | ≧50 | ≧50 | 20 |
| Adhesion 1) | 100/100 | 100/100 | 100/100 | 100/100 | 0/100 |

What is claimed is:

1. A method for preparing an α-(aminocyclohexyl)alkylamine represented by the following formula (II):

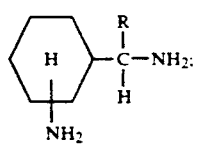

(II)

wherein R represents a hydrogen atom or a lower alkyl group having 1 to 5 carbon atoms, and the amino group bonded to the cyclohexyl group may be in either of the 2-, 3- and 4-positions, said process comprising catalytically reducing an α-(aminophenyl)alkylamine represented by the following formula (I);

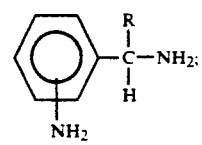

(I)

wherein R represents a hydrogen atom or a lower alkyl group having 1 to 5 carbon atoms, and the amino group bonded to the phenyl group may be in either of the 2-, 3- and 4-positions, in the presence of a ruthenium catalyst, water or 1,4-dioxane, and an alkali or alkaline earth metal hydroxide.

2. An α-(aminocyclohexyl)alkylamine represented by the following formula (II'):

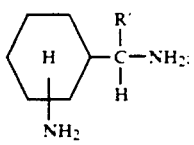

(II')

where R' represents a lower alkyl group having 2 to 5 carbon atoms, and the amino group bonded to the cyclohexyl group may be in either of the 2-, 3- and 4-positions.

3. An α-(aminocyclohexyl)alkylamine represented by the following formula (II''):

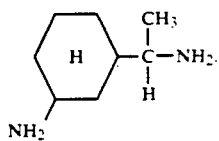

(II'')

4. A method according to claim 1, wherein the α-(aminocyclohexyl)alkylamine of formula (II) is prepared by catalytically reducing an α-(aminophenyl)alkylamine of formula (I) in the presence of a ruthenium catalyst, water, and an alkali or alkaline earth metal hydroxide.

5. A method according to claim 4, said water being present in an amount of 1–40 wt % based on the amount of α-(aminophenyl)alkylamine.

* * * * *